(12) United States Patent
Vorobiev et al.

(10) Patent No.: US 9,085,800 B2
(45) Date of Patent: Jul. 21, 2015

(54) FUNCTIONALIZED 3-ALKYNYL PYRAZOLOPYRIMIDINE ANALOGUES AS UNIVERSAL BASES AND METHODS OF USE

(75) Inventors: Alexei Vorobiev, Redmond, WA (US); Eugeny A. Lukhtanov, Bothell, WA (US); Noah Scarr, Seattle, WA (US)

(73) Assignee: Elitech Holding B.V., Spankeren (NL)

(*) Notice: Subject to any disclaimer, the term of this patent is extended or adjusted under 35 U.S.C. 154(b) by 36 days.

(21) Appl. No.: 13/429,273

(22) Filed: Mar. 23, 2012

(65) Prior Publication Data

US 2012/0244535 A1    Sep. 27, 2012

Related U.S. Application Data

(60) Provisional application No. 61/466,755, filed on Mar. 23, 2011.

(51) Int. Cl.
*C12Q 1/68* (2006.01)
*C07H 21/04* (2006.01)

(52) U.S. Cl.
CPC ............ *C12Q 1/6853* (2013.01); *C12Q 1/6846* (2013.01); *C12Q 2525/117* (2013.01)

(58) Field of Classification Search
CPC ............... C12Q 1/6844; C12Q 1/6853; C12Q 2525/117
USPC ........................ 435/6.1, 6.11, 6.12; 536/24.33
See application file for complete search history.

(56) References Cited

U.S. PATENT DOCUMENTS

| | | | |
|---|---|---|---|
| 3,996,345 A | 12/1976 | Ullman et al. | |
| 4,351,760 A | 9/1982 | Khanna et al. | |
| 5,177,196 A | 1/1993 | Meyer, Jr. et al. | |
| 5,419,966 A | 5/1995 | Reed et al. | |
| 5,492,806 A | 2/1996 | Drmanac et al. | |
| 5,512,677 A | 4/1996 | Chern et al. | |
| 5,525,464 A | 6/1996 | Drmanac et al. | |
| 5,539,082 A | 7/1996 | Nielsen et al. | |
| 5,556,752 A | 9/1996 | Lockhart et al. | |
| 5,585,481 A | 12/1996 | Arnold, Jr. et al. | |
| 5,696,251 A | 12/1997 | Arnold, Jr. et al. | |
| 5,714,331 A | 2/1998 | Buchardt et al. | |

(Continued)

FOREIGN PATENT DOCUMENTS

EP    1944310    7/2008
WO    92/10588    6/1992

(Continued)

OTHER PUBLICATIONS

Crick, F.H.C.; Codon-Anticodon Pairing: The Wobble Hypothesis; J. Mol. Biol., 19, 548-555, 1966.

(Continued)

*Primary Examiner* — Jezia Riley
(74) *Attorney, Agent, or Firm* — Jackson Walker L.L.P.

(57) ABSTRACT

3-alkynyl inosine analogs and their uses as universal bases are provided. The inosine analogues can be incorporated into nucleic acid primers and probes. They do not significantly destabilize nucleic acid duplexes. As a result, the novel nucleic acid primers and probes incorporating the inosine analogues can be used in a variety of methods. The analogs function unexpectedly well as universal bases. Not only do they stabilize duplexes substantially more than hypoxanthine opposite A, C, T, and G but they are also recognized in primers by polymerases, allowing efficient amplification.

12 Claims, 17 Drawing Sheets

(56) References Cited

U.S. PATENT DOCUMENTS

| | | | |
|---|---|---|---|
| 5,736,626 | A | 4/1998 | Mullah et al. |
| 5,766,855 | A | 6/1998 | Buchardt et al. |
| 5,773,571 | A | 6/1998 | Nielsen et al. |
| 5,801,155 | A | 9/1998 | Kutyavin et al. |
| 6,312,894 | B1 | 11/2001 | Hedgpeth et al. |
| RE38,416 | E | 2/2004 | Petrie et al. |
| 6,727,356 | B1 | 4/2004 | Reed et al. |
| 6,790,945 | B2 | 9/2004 | Lukhtanov et al. |
| 7,045,610 | B2 | 5/2006 | Dempcy et al. |
| 7,319,022 | B1 | 1/2008 | Mahoney et al. |
| 7,348,146 | B2 | 3/2008 | Belousov et al. |

FOREIGN PATENT DOCUMENTS

| | | |
|---|---|---|
| WO | 96/17957 | 6/1996 |
| WO | 03/062445 | 7/2003 |
| WO | 2005/043127 | 5/2005 |

OTHER PUBLICATIONS

Lee, H., et al; Next-Generation Sequencing Technologies and Fragment Assembly Algorithms; Methods in Molecular Biology, vol. 855, 155-174, 2012.

Loakes, D., et al; Stability and Structure of DNA Oligonucleotides Containing Non-Specific Base Analogues; J. Mol. Biol., 270, 426-435, 1997.

Nielsen, P.E., et al; Sequence-Selective Recognition of DNA by Strand Displacement With a Thymine-Substituted Polyamide; Science, 254, 1497-1500, 1991.

Wengel, J.; Synthesis of 3'-C- and 4'-C-Branched Oligonucleotides and the Development of Locked Nucleic Acid (LNA); Acc. Chem. Res., 32, 301-310, 1999.

European Patent Office; International Search Report and Written Opinion; PCT Application No. PCT/US2012/030467; Jul. 19, 2012.

Qing, G., et al; Spatially Controlled DNA Nanopatterns by "Click" Chemistry Using Oligonucleotides With Different Anchoring Sites; J. Am. Chem. Soc., 132, 15228-15232, Nov. 3, 2010.

He, J., et al; Propynyl Groups in Duplex DNA: Stability of Base Pairs Incorporating 7-Substituted 8-Aza-7-Deazapurines or 5-Substituted Pyrimidines; Nucleic Acids Research, vol. 30, No. 24, 5485-5496, Dec. 15, 2002.

Pujari, S., et al; Cross-Linked DNA Generated by "Bis-Click" Reactions With Bis-Functional Azides: Site Independent Ligation of Oligonucleotides via Nucleobase Alkynyl Chains; Journal of Organic Chemistry, vol. 75, No. 24, 8693-8696, Dec. 17, 2010.

Seela, F., et al; Oligonucleotides Containing Pyrazolo[3,4-d]Pyrimidines: The Influence of 7-Substituted 8-Aza-7-Deaza-2'-Deoxyguanosines on the Duplex Structure and Stability; Helvetica Chimica Acta, vol. 82, 1640-1655, Jan. 1, 1999.

Seela, F., et al; Synthesis and 'Double Click' Density Functionalization of 8-Aza-7-Deazaguanine DNA Bearing Branched Side Chains With Terminal Triple Bonds; Tetrahedron, vol. 66, No. 22, 3930-3943, May 1, 2010.

Beaucage, S.L., et al; Advances in the Synthesis of Oligonucleotides by the Phosphoramidite Approach; Tetrahedron, vol. 48, No. 12, 2223-2311, 1992.

Bergstrom, D.E., et al; Comparison of the Base Pairing Properties of a Series of Nitroazole Nucleobase Analogs in the Oligodeoxyribonucleotide Sequence; 5'-d(CGCXAATTYGCG)-3', Nucleic Acids Research, vol. 25, No. 10, 1935-1942, 1997.

Chen, Jer-Kang, et al; Synthesis of Oligodeoxyribonucleotide N3'-P5' Phosphoramidates; Nucleic Acids Research, vol. 23, No. 14, 2661-2668, 1995.

Greene, T.W., et al; Protective Groups in Organic Synthesis, John Wiley & Sons, 1991.

Haugland, R.P., Handbook of Fluorescent Probes and Research Chemicals, Sixth Edition, Molecular Probes, 3 pages,1996.

Loakes, D.; Survey and Summary: The Applications of Universal DNA Base Analogues; Nucleic Acids Research, vol. 29, No. 12, 2437-2447, 2001.

Ming, X., et al; Azide-Alkyne "Click" Reaction Performed on Oligonucleotides With the Universal Nucleoside 7-Octadiynyl-7-Deaza-2'-Deoxyinosine; Nucleic Acids Symposium Series No. 52, 471-472, 2008.

Niemz, A., et al; Point-of-Care Nucleic Acid Testing for Infectious Diseases, Trends in Biotechnology, 11 pages, 2011.

Palissa, M., et al; Reduction of Protected 2'-Chloro-2'-Deoxy-Dinucleotides With Tri-N-Butyltinhydride; Z. Chem., 27, 216, 1987.

Sambrook, J., et al; Molecular Cloning: A Laboratory Manual, Second Edition, Cold Spring Harbor Laboratory Press, 1989.

Reddy, B.S. Praveen, et al; Synthetic DNA Minor Groove-Binding Drugs; Pharmacology & Therapeutics 84, 1-111, 1999.

Singh, Sanjay K., et al; LNA (Locked Nucleic Acids): Synthesis and High-Affinity Nucleic Acid Recognition; Chem. Comm., 455-456, 1998.

Uhlmann, E., et al; PNA: Synthetic Polyamide Nucleic Acids With Unusual Binding Properties; Angew. Chem. Int. Ed., 37, 2797-2823, 1998.

Walker, W.L., et al; Progress in the Design of DNA Sequence-Specific Lexitropsins; Biopolymers, 44, 323-334, 1997.

Watkins, N.E., Jr., et al; Nearest-Neighbor Thermodynamics of Deoxyinosine Pairs in DNA Duplexes; Nucleic Acids Research, vol. 33, No. 19, 6258-6267, 2005.

Wemmer, D.E., et al; Targeting the Minor Groove of DNA, Current Opinion in Structural Biology, 7, 355-361, 1997.

Zimmer, Christopher ,et al; Nonintercalating DNA-Binding Ligands: Specificity of the Interaction and Their Use as Tools in Biophysical, Biochemical and Biological Investigations of the Genetic Material; Prog. Biophys. Molec. Bio. 47, 31-112, 1986.

European Patent Office; International Search Report and Written Opinion; PCT Application No. PCT/US2014/021799; Jul. 15, 2014.

International Bureau of WIPO; Art. 19 Amendments; PCT Application No. PCT/US2014/021799; Aug. 29, 2014.

Kumar; Pawan et al; Three Pyrene-Modified Nucleotides: Synthesis and Effects in Secondary Nucleic Acid Structures; The Journal of Organic Chemistry; vol. 77, No. 21, Nov. 2, 2012.

European Patent Office; Office Action; European Application No. 12712197.8; Jul. 8, 2014.

European Patent Office; Response to Office Action; European Application No. 12712197.8; Nov. 14, 2014.

Figure 10

| Sequence1 (5'-3') | Sequence2 (5'-3') | SEQ ID NO. | position | pair | match | X=dI |
|---|---|---|---|---|---|---|
| GTAAGXAGACATAAC | AAAGTTATGTCTACTTACAGAAA | 49 | 6 | X/A | 54.0 | 51.7 |
| GTAAGXAGACATAAC | AAAGTTATGTCTTCTTACAGAAA | 50 | 6 | X/T | 54.0 | 47.3 |
| GTAAGXAGACATAAC | AAAGTTATGTCTCCTTACAGAAA | 51 | 6 | X/C | 56.3 | 52.3 |
| GTAAGXAGACATAAC | AAAGTTATGTCTGCTTACAGAAA | 52 | 6 | X/G | 57.7 | 47.0 |
| GTAAGTAGXCATAAC | AAAGTTATGTCTACTTACAGAAA | 49 | 9 | X/T | 54.3 | 53.1 |
| GTAAGTAGXCATAAC | AAAGTTATGACTACTTACAGAAA | 53 | 9 | X/A | 54.0 | 47.9 |
| GTAAGTAGXCATAAC | AAAGTTATGCCTACTTACAGAAA | 54 | 9 | X/C | 57.3 | 52.3 |
| GTAAGTAGXCATAAC | AAAGTTATGGCTACTTACAGAAA | 55 | 9 | X/G | 57.4 | 49.1 |
| GTAAGXAGXCATAAC | AAAGTTATGTCTACTTACAGAAA | 49 | 6+9 | X/T, X/A | 54.0 | 46.1 |
| GTAAGXAGXCATAAC | AAAGTTATGTCTTCTTACAGAAA | 50 | 6+9 | X/T, X/T | 54.0 | 41.6 |
| GTAAGXAGXCATAAC | AAAGTTATGTCTCCTTACAGAAA | 51 | 6+9 | X/T, X/C | 56.3 | 46.4 |
| GTAAGXAGXCATAAC | AAAGTTATGTCTGCTTACAGAAA | 52 | 6+9 | X/T, X/G | 57.7 | 41.2 |
| GTAAGXAGXCATAAC | AAAGTTATGACTACTTACAGAAA | 53 | 6+9 | X/A, X/A | 54.3 | 51.1 |
| GTAAGXAGXCATAAC | AAAGTTATGCCTACTTACAGAAA | 54 | 6+9 | X/C, X/A | 57.3 | 50.8 |
| GTAAGXAGXCATAAC | AAAGTTATGGCTACTTACAGAAA | 55 | 6+9 | X/G, X/A | 57.4 | 47.4 |
| GTAAGXAGXCATAAC | AAAGTTATGACTTCTTACAGAAA | 56 | 6+9 | X/A, X/T | 54.6 | 46.9 |
| GTAAGXAGXCATAAC | AAAGTTATGCCTTCTTACAGAAA | 57 | 6+9 | X/C, X/T | 57.3 | 46.8 |
| GTAAGXAGXCATAAC | AAAGTTATGGCTTCTTACAGAAA | 58 | 6+9 | X/G, X/T | 57.5 | 43.1 |
| GTAAGXAGXCATAAC | AAAGTTATGACTCCTTACAGAAA | 59 | 6+9 | X/A, X/C | 56.2 | 51.6 |
| GTAAGXAGXCATAAC | AAAGTTATGCCTCCTTACAGAAA | 60 | 6+9 | X/C, X/C | 59.6 | 51.5 |
| GTAAGXAGXCATAAC | AAAGTTATGGCTCCTTACAGAAA | 61 | 6+9 | X/G, X/C | 59.8 | 47.6 |
| GTAAGXAGXCATAAC | AAAGTTATGACTGCTTACAGAAA | 62 | 6+9 | X/A, X/G | 58.1 | 46.7 |
| GTAAGXAGXCATAAC | AAAGTTATGCCTGCTTACAGAAA | 63 | 6+9 | X/C, X/G | 60.7 | 46.6 |
| GTAAGXAGXCATAAC | AAAGTTATGGCTGCTTACAGAAA | 64 | 6+9 | X/G, X/G | 61.4 | 42.6 |

| X=I04 | X=I06 | X=I07 | X=I08 | X=I09 | X=I10 | X=I11 | X=I4g | X=I6g | X=I12 |
|---|---|---|---|---|---|---|---|---|---|
| 52.9 | 53.1 | 53.8 | 53.7 | 53.4 | 52.1 | 52.5 | 54.8 | 53.3 | 52.7 |
| 48.7 | 50.2 | 53.2 | 53.1 | 51.0 | 47.8 | 48.4 | 51.5 | 49.3 | 48.8 |
| 53.8 | 54.4 | 55.1 | 54.8 | 54.2 | 52.9 | 53.5 | 55.9 | 54.6 | 53.9 |
| 45.4 | 45.9 | 47.3 | 46.5 | 46.1 | 44.9 | 45.2 | 47.0 | 46.3 | 45.9 |
| 54.8 | 55.6 | 57.4 | 56.8 | 55.8 | 54.2 | 55.6 | 56.7 | 56.2 | 55.1 |
| 50.1 | 51.7 | 55.9 | 56.0 | 52.7 | 49.1 | 50.6 | 54.0 | 51.6 | 50.3 |
| 55.0 | 55.9 | 57.5 | 56.6 | 55.8 | 54.0 | 55.1 | 56.9 | 56.2 | 55.2 |
| 47.3 | 47.6 | 49.4 | 48.3 | 47.7 | 47.1 | 47.7 | 48.3 | 48.3 | 47.2 |
| 48.8 | 51.0 | 56.2 | 55.8 | 52.1 | 47.3 | 48.8 | 52.5 | N/T | N/T |
| 44.3 | 48.0 | 55.2 | 54.7 | 49.0 | 42.4 | 44.5 | 48.6 | N/T | N/T |
| 50.0 | 51.8 | 57.2 | 56.3 | 52.7 | 48.5 | 49.7 | 53.6 | N/T | N/T |
| 40.8 | 43.0 | 49.9 | 48.2 | 44.1 | 40.2 | 41.5 | 44.4 | N/T | N/T |
| 54.1 | 55.0 | 57.9 | 57.4 | 55.4 | 52.5 | 54.6 | 57.1 | N/T | N/T |
| 54.0 | 55.1 | 58.2 | 56.8 | 55.1 | 52.4 | 53.7 | 57.0 | N/T | N/T |
| 46.3 | 47.5 | 49.5 | 48.6 | 46.9 | 45.6 | 46.4 | 48.5 | N/T | N/T |
| 49.7 | 51.8 | 57.2 | 56.4 | 52.5 | 47.3 | 50.0 | 52.8 | N/T | N/T |
| 49.8 | 52.5 | 57.3 | 56.2 | 52.8 | 47.7 | 49.3 | 53.4 | N/T | N/T |
| 41.4 | 43.9 | 48.5 | 47.6 | 44.0 | 39.5 | 42.0 | 44.3 | N/T | N/T |
| 55.0 | 56.3 | 58.6 | 58.1 | 56.3 | 53.1 | 55.6 | 57.8 | N/T | N/T |
| 54.7 | 56.1 | 58.7 | 56.9 | 55.8 | 53.2 | 54.8 | 57.9 | N/T | N/T |
| 47.3 | 48.4 | 50.6 | 49.4 | 47.9 | 46.3 | 47.7 | 50.1 | N/T | N/T |
| 46.5 | 47.6 | 51.0 | 49.8 | 47.9 | 45.5 | 47.5 | 49.6 | N/T | N/T |
| 46.7 | 47.8 | 51.7 | 49.4 | 47.8 | 45.5 | 46.6 | 49.7 | N/T | N/T |
| 38.1 | 38.8 | 42.3 | 40.4 | 38.6 | 37.6 | 38.6 | 39.9 | N/T | N/T |

N/T - not tested

Figure 14

| Forward primer | Sequence (5'-3') | SEQ ID NO. | pair | Tm | Ct (65/95°C) | Ct (70/95°C) |
|---|---|---|---|---|---|---|
| ADV-1 | GGCCCGAGATG(dI)GCATGTA | 4 | dI/A | 67.7 | 25 | 25.5 |
| ADV-2 | GGCCCGAGATGT(dI)CATGTA | 5 | dI/C | 65.4 | 24 | ave: 32 |
| ADV-3 | GGCCCGAGATGTG(dI)ATGTA | 6 | dI/G | 61.2 | 25 | ave: 45 |
| ADV-4 | GGCCCGAGATGTGC(dI)TGTA | 7 | dI/T | 65.9 | 24 | 31 |
| ADV-5 | GGCCCGAGATG(I04)GCATGTA | 8 | I04/A | 68.3 | 25 | 26 |
| ADV-6 | GGCCCGAGATGT(I04)CATGTA | 9 | I04/C | 67.9 | 24 | 25 |
| ADV-7 | GGCCCGAGATGTG(I04)ATGTA | 10 | I04/G | 60.5 | 28 | 37 |
| ADV-8 | GGCCCGAGATGTGC(I04)TGTA | 11 | I04/T | 67.1 | 24 | 26.5 |
| ADV-9 | GGCCCGAGATG(I07)GCATGTA | 12 | I07/A | 68.9 | 24 | 25 |
| ADV-10 | GGCCCGAGATGT(I07)CATGTA | 13 | I07/C | 67.4 | 24 | 24 |
| ADV-11 | GGCCCGAGATGTG(I07)ATGTA | 14 | I07/G | 61.4 | 25.5 | 31 |
| ADV-12 | GGCCCGAGATGTGC(I07)TGTA | 15 | I07/T | 66.5 | 24.5 | 26 |
| ADV-L1 | GGCCCGAGATGTGCATGTA | 16 | match | 69.7 | 24 | 24 |
| ADV-C | TACATGCACATCTCGGGCC | 17 | complement | | | |

Reverse primer Sequence (5'-3')
ADV-MGB-FAM    MGB-FAM-AATAAATCATAAGATCGCTACCCCTTCGA (SEQ ID NO.: 18)

AATAAATCATAA (SEQ ID NO.: 19) - target non-specific flap sequence

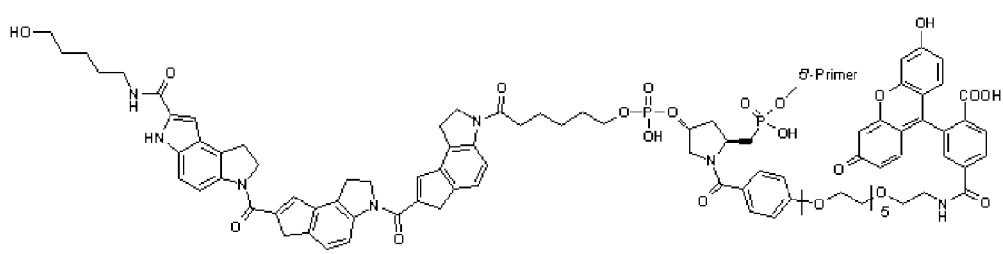

Figure 15

| Forward primer | Sequence (5'-3') | SEQ ID NO. | mismatch | Tm | Ct (65/95oC) |
|---|---|---|---|---|---|
| ADV-25 | GGCCCGAGATG(dI)G(dI)ATGTA | 20 | dI/A, dI/G | 59.5 | 26 |
| ADV-26 | GGCCCGAGATG(dI)GC(dI)TGTA | 21 | dI/A, dI/T | 63.7 | 25.5 |
| ADV-27 | GGCCCGAGATG(dI)GCA(dI)GTA | 22 | dI/A, dI/A | 66.1 | 27 |
| ADV-28 | GGCCCGAGATG(dI)GCAT(dI)TA | 23 | dI/A, dI/C | 65.4 | 24 |
| ADV-13 | GGCCCGAGATG(I04)G(I04)ATGTA | 24 | I04/A, I04/G | 58.6 | 28 |
| ADV-14 | GGCCCGAGATG(I04)GC(I04)TGTA | 25 | I04/A, I04/T | 64.7 | 25 |
| ADV-15 | GGCCCGAGATG(I04)GCA(I04)GTA | 26 | I04/A, I04/A | 66.2 | 26 |
| ADV-16 | GGCCCGAGATG(I04)GCAT(I04)TA | 27 | I04/A, I04/C | 66.0 | 24 |
| ADV-17 | GGCCCGAGATG(I07)G(I07)ATGTA | 28 | I07/A, I07/G | 62.1 | 27 |
| ADV-18 | GGCCCGAGATG(I07)GC(I07)TGTA | 29 | I07/A, I07/T | 66.6 | 24 |
| ADV-19 | GGCCCGAGATG(I07)GCA(I07)GTA | 30 | I07/A, I07/A | 67.3 | 25 |
| ADV-20 | GGCCCGAGATG(I07)GCAT(I07)TA | 31 | I07/A, I07/C | 66.6 | 23 |
| ADV-29 | GGCCCGAGATGTGCATG(dI)A | 32 | dI/A | 68.3 | 34 |
| ADV-30 | GGCCCGAGATGTGCATGT(dI) | 33 | dI/T | 68.4 | 32 |
| ADV-21 | GGCCCGAGATGTGCATG(I04)A | 34 | I04/A | 68.6 | 42 |
| ADV-22 | GGCCCGAGATGTGCATGT(I04) | 35 | I04/T | 68.6 | nothing |
| ADV-23 | GGCCCGAGATGTGCATG(I07)A | 36 | I07/A | 68.6 | 37 |
| ADV-24 | GGCCCGAGATGTGCATGT(I07) | 37 | I07/T | 68.6 | 43 |
| ADV-32 | GGCCCGAC(dI)TG(dI)GC(dI)TGTA | 38 | dI/A, dI/T, dI/T | 58.5 | 30 |
| ADV-31 | GGCCCGAGA(dI)G(dI)GC(dI)TGTA | 39 | dI/A, dI/T, dI/A | 61.0 | 31 |
| ADV-34 | GGCCCGAG(I04)TG(I04)GC(I04)TGTA | 40 | I04/A, I04/T, I04/T | 61.4 | 28 |
| ADV-33 | GGCCCGAGA(I04)G(I04)GC(I04)TGTA | 41 | I04/A, I04/T, I04/A | 62.9 | 26 |
| ADV-36 | GGCCCGAG(I07)TG(I07)GC(I07)TGTA | 42 | I07/A, I07/T, I07/T | 63.9 | 24 |
| ADV-35 | GGCCCGAGA(I07)G(I07)GC(I07)TGTA | 43 | I07/A, I07/T, I07/A | 65.4 | 24 |

Figure 16

| | Sequence (5'-3") | Mismatch | Ct (56°C) | Ct (56°C) |
|---|---|---|---|---|
| LGA-L23 | GTATATTTCCGTTATTTTCTAAAGCACT (SEQ ID NO.: 44) | none | 35 | 33 |
| LGA-L24 | GTATA(dI)TTCCGTTA(dI)TT(dI)CT(dI)A(dI)GCACT (SEQ ID NO.: 45) | 3xdI/A, 2xdI/T | 42 | none |
| LGA-L25 | GTATA(I07)TTCCGTTA(I07)TT(I07)CT(I07)A(I07)GCACTG (SEQ ID NO.: 46) | 3xI07/A, 2xI07/T | 36 | 36 |

| LGA-E3 | AATAAATCATAAGGCCAAGGCGAGATACTAGTAAACC (SEQ ID NO.: 47) (excess primer) | 1.260 µM |
|---|---|---|
| LGA-FAM5 | MGB-FAM-G*ATAAA*AT*T*T*GTA*TA*GG-EDQ (SEQ ID NO.: 48) (detection probe) | 0.200 µM |

G* is Super G, A* is Super A, T* is Super T
MGB - Minor Groove Binder,
FAM - 6-Carboxyfluorescein
EDQ - Eclipse Dark Quencher

Figure 17

Sequences of PCR products generated from inosine primers:

Target sequence (primer regions are shown in italics; T base to be replaced in primer shown in bold):

5'ACAT*gaggattttgtatatttccgtta**tttt**ctaaagcactg*TATATTGATAAAATTTGTAT
AG*ggtttactagtatctcgccttggcc*AT   (SEQ ID NO.: 65)

Primers:

| | |
|---|---|
| Natural F primer | 5'GAGGATTTTGTATATTTCCGTTATTTTCTAAAGCACTG 3'<br>(SEQ ID NO.: 66) |
| F(I01)primer | 5'GAGGATTTTGTATATTTCCGTTA**(dI)TT(dI)**CTAAAGCACTG 3'<br>(SEQ ID NO.: 67) |
| F(I07)primer | 5'GAGGATTTTGTATATTTCCGTTA(I07)TT(I07)CTAAAGCACTG 3'<br>(SEQ ID NO.: 68) | where (dI) is inosine

Amplicon sequencing results:

Natural F primer (reverse strand):
3'CAGTGCTTTAGAAAATAACGGAAATATACAAAATCCTC     5'
(SEQ ID NO.: 69)

Amplicon complimentary to F(dI)primer:
3'CAGNGCTTTAGCAACTAACGGAAATATACAAAANNCTC     5'
(SEQ ID NO.: 70)

Amplicon complimentary to F(I07)primer:
3'CANNNCTTTAGCAACTAACGGAAANATACAAAATCCTN     5'
(SEQ ID NO.: 71)

SEQUENCE LISTING

<160> NUMBER OF SEQ ID NOS: 71

<210> SEQ ID NO 1
<211> LENGTH: 15
<212> TYPE: DNA
<213> ORGANISM: Artificial Sequence
<220> FEATURE:
<223> OTHER INFORMATION: Duplex
<220> FEATURE:
<221> NAME/KEY: misc_feature
<222> LOCATION: (6)..(6)
<223> OTHER INFORMATION: n is 2'-deoxyinosine or 2-deoxy-
      -D-ribofuranosyl-3-alkynyl-1H-pyrazolo[3,4-d]pyrimidin-4(5H)-one
<220> FEATURE:
<221> NAME/KEY: misc_feature
<222> LOCATION: (9)..(9)
<223> OTHER INFORMATION: n is 2'-deoxyinosine or 2-deoxy-
      -D-ribofuranosyl-3-alkynyl-1H-pyrazolo[3,4-d]pyrimidin-4(5H)-one

<400> SEQUENCE: 1
gtaagnagnc ataac                                                    15

<210> SEQ ID NO 2
<211> LENGTH: 15
<212> TYPE: DNA
<213> ORGANISM: Artificial Sequence
<220> FEATURE:
<223> OTHER INFORMATION: Duplex
<220> FEATURE:
<221> NAME/KEY: misc_feature
<222> LOCATION: (6)..(6)
<223> OTHER INFORMATION: n is 2'-deoxyinosine or 2-deoxy-
      -D-ribofuranosyl-3-alkynyl-1H-pyrazolo[3,4-d]pyrimidin-4(5H)-one

<400> SEQUENCE: 2
gtaagnagac ataac                                                    15

<210> SEQ ID NO 3
<211> LENGTH: 15
<212> TYPE: DNA
<213> ORGANISM: Artificial Sequence
<220> FEATURE:
<223> OTHER INFORMATION: Duplex
<220> FEATURE:
<221> NAME/KEY: misc_feature
<222> LOCATION: (9)..(9)
<223> OTHER INFORMATION: n is 2'-deoxyinosine or 2-deoxy-
      -D-ribofuranosyl-3-alkynyl-1H-pyrazolo[3,4-d]pyrimidin-4(5H)-one

<400> SEQUENCE: 3
gtaagtagnc ataac                                                    15

<210> SEQ ID NO 4
<211> LENGTH: 19
<212> TYPE: DNA
<213> ORGANISM: Artificial Sequence
<220> FEATURE:
<223> OTHER INFORMATION: ADV-1 primer
<220> FEATURE:
<221> NAME/KEY: misc_feature
<222> LOCATION: (12)..(12)
<223> OTHER INFORMATION: n is dI

<400> SEQUENCE: 4
ggcccgagat gngcatgta                                                19

<210> SEQ ID NO 5
<211> LENGTH: 19
<212> TYPE: DNA
<213> ORGANISM: Artificial Sequence

```
<220> FEATURE:
<223> OTHER INFORMATION: ADV-2 primer
<220> FEATURE:
<221> NAME/KEY: misc_feature
<222> LOCATION: (13)..(13)
<223> OTHER INFORMATION: n is dI

<400> SEQUENCE: 5
ggcccgagat gtncatgta                                               19

<210> SEQ ID NO 6
<211> LENGTH: 19
<212> TYPE: DNA
<213> ORGANISM: Artificial Sequence
<220> FEATURE:
<223> OTHER INFORMATION: ADV-3 primer
<220> FEATURE:
<221> NAME/KEY: misc_feature
<222> LOCATION: (14)..(14)
<223> OTHER INFORMATION: n is dI

<400> SEQUENCE: 6
ggcccgagat gtgnatgta                                               19

<210> SEQ ID NO 7
<211> LENGTH: 19
<212> TYPE: DNA
<213> ORGANISM: Artificial Sequence
<220> FEATURE:
<223> OTHER INFORMATION: ADV-4
<220> FEATURE:
<221> NAME/KEY: misc_feature
<222> LOCATION: (15)..(15)
<223> OTHER INFORMATION: n is dI

<400> SEQUENCE: 7
ggcccgagat gtgcntgta                                               19

<210> SEQ ID NO 8
<211> LENGTH: 19
<212> TYPE: DNA
<213> ORGANISM: Artificial Sequence
<220> FEATURE:
<223> OTHER INFORMATION: ADV-5 primer
<220> FEATURE:
<221> NAME/KEY: misc_feature
<222> LOCATION: (12)..(12)
<223> OTHER INFORMATION: n is I04

<400> SEQUENCE: 8
ggcccgagat gngcatgta                                               19

<210> SEQ ID NO 9
<211> LENGTH: 19
<212> TYPE: DNA
<213> ORGANISM: Artificial Sequence
<220> FEATURE:
<223> OTHER INFORMATION: ADV-6 primer
<220> FEATURE:
<221> NAME/KEY: misc_feature
<222> LOCATION: (13)..(13)
<223> OTHER INFORMATION: n is I04

<400> SEQUENCE: 9
ggcccgagat gtncatgta                                               19

<210> SEQ ID NO 10
<211> LENGTH: 19
<212> TYPE: DNA
```

```
<213> ORGANISM: Artificial Sequence
<220> FEATURE:
<223> OTHER INFORMATION: ADV-7 primer
<220> FEATURE:
<221> NAME/KEY: misc_feature
<222> LOCATION: (14)..(14)
<223> OTHER INFORMATION: n is I04

<400> SEQUENCE: 10
ggcccgagat gtgnatgta                                                         19

<210> SEQ ID NO 11
<211> LENGTH: 19
<212> TYPE: DNA
<213> ORGANISM: Artificial Sequence
<220> FEATURE:
<223> OTHER INFORMATION: ADV-8 primer
<220> FEATURE:
<221> NAME/KEY: misc_feature
<222> LOCATION: (15)..(15)
<223> OTHER INFORMATION: n is I04

<400> SEQUENCE: 11
ggcccgagat gtgcntgta                                                         19

<210> SEQ ID NO 12
<211> LENGTH: 19
<212> TYPE: DNA
<213> ORGANISM: Artificial Sequence
<220> FEATURE:
<223> OTHER INFORMATION: ADV-9 primer
<220> FEATURE:
<221> NAME/KEY: misc_feature
<222> LOCATION: (12)..(12)
<223> OTHER INFORMATION: n is I07

<400> SEQUENCE: 12
ggcccgagat gngcatgta                                                         19

<210> SEQ ID NO 13
<211> LENGTH: 19
<212> TYPE: DNA
<213> ORGANISM: Artificial Sequence
<220> FEATURE:
<223> OTHER INFORMATION: ADV-10
<220> FEATURE:
<221> NAME/KEY: misc_feature
<222> LOCATION: (13)..(13)
<223> OTHER INFORMATION: n is I07

<400> SEQUENCE: 13
ggcccgagat gtncatgta                                                         19

<210> SEQ ID NO 14
<211> LENGTH: 19
<212> TYPE: DNA
<213> ORGANISM: Artificial Sequence
<220> FEATURE:
<223> OTHER INFORMATION: ADV-11 primer
<220> FEATURE:
<221> NAME/KEY: misc_feature
<222> LOCATION: (14)..(14)
<223> OTHER INFORMATION: n is I07

<400> SEQUENCE: 14
ggcccgagat gtgnatgta                                                         19

<210> SEQ ID NO 15
<211> LENGTH: 19
```

```
<212> TYPE: DNA
<213> ORGANISM: Artificial Sequence
<220> FEATURE:
<223> OTHER INFORMATION: ADV-12 primer
<220> FEATURE:
<221> NAME/KEY: misc_feature
<222> LOCATION: (15)..(15)
<223> OTHER INFORMATION: n is I07

<400> SEQUENCE: 15
ggcccgagat gtgcntgta                                            19

<210> SEQ ID NO 16
<211> LENGTH: 19
<212> TYPE: DNA
<213> ORGANISM: Artificial Sequence
<220> FEATURE:
<223> OTHER INFORMATION: ADV-L1 primer

<400> SEQUENCE: 16
ggcccgagat gtgcatgta                                            19

<210> SEQ ID NO 17
<211> LENGTH: 19
<212> TYPE: DNA
<213> ORGANISM: Artificial Sequence
<220> FEATURE:
<223> OTHER INFORMATION: ADV-L1

<400> SEQUENCE: 17
tacatgcaca tctcgggcc                                            19

<210> SEQ ID NO 18
<211> LENGTH: 29
<212> TYPE: DNA
<213> ORGANISM: Artificial Sequence
<220> FEATURE:
<223> OTHER INFORMATION: ADV-MGB-FAM primer
<220> FEATURE:
<221> NAME/KEY: misc_feature
<222> LOCATION: (1)..(1)
<223> OTHER INFORMATION: n is A conjugated to FAM and minor groove
      binder (MGB)

<400> SEQUENCE: 18
nataaatcat aagatggcta ccccttcga                                 29

<210> SEQ ID NO 19
<211> LENGTH: 12
<212> TYPE: DNA
<213> ORGANISM: Artificial Sequence
<220> FEATURE:
<223> OTHER INFORMATION: target non-specific flap sequence

<400> SEQUENCE: 19
aataaatcat aa                                                   12

<210> SEQ ID NO 20
<211> LENGTH: 19
<212> TYPE: DNA
<213> ORGANISM: Artificial Sequence
<220> FEATURE:
<223> OTHER INFORMATION: ADV-25 primer
<220> FEATURE:
<221> NAME/KEY: misc_feature
<222> LOCATION: (12)..(12)
<223> OTHER INFORMATION: n is dI
<220> FEATURE:
<221> NAME/KEY: misc_feature
```

```
<222> LOCATION: (14)..(14)
<223> OTHER INFORMATION: n is dI

<400> SEQUENCE: 20
ggcccgagat gngnatgta                                              19

<210> SEQ ID NO 21
<211> LENGTH: 19
<212> TYPE: DNA
<213> ORGANISM: Artificial Sequence
<220> FEATURE:
<223> OTHER INFORMATION: ADV-26 primer
<220> FEATURE:
<221> NAME/KEY: misc_feature
<222> LOCATION: (12)..(12)
<223> OTHER INFORMATION: n is dI
<220> FEATURE:
<221> NAME/KEY: misc_feature
<222> LOCATION: (15)..(15)
<223> OTHER INFORMATION: n is dI

<400> SEQUENCE: 21
ggcccgagat gngcntgta                                              19

<210> SEQ ID NO 22
<211> LENGTH: 19
<212> TYPE: DNA
<213> ORGANISM: Artificial Sequence
<220> FEATURE:
<223> OTHER INFORMATION: ADV-27 primer
<220> FEATURE:
<221> NAME/KEY: misc_feature
<222> LOCATION: (12)..(12)
<223> OTHER INFORMATION: n is dI
<220> FEATURE:
<221> NAME/KEY: misc_feature
<222> LOCATION: (16)..(16)
<223> OTHER INFORMATION: n is dI

<400> SEQUENCE: 22
ggcccgagat gngcangta                                              19

<210> SEQ ID NO 23
<211> LENGTH: 19
<212> TYPE: DNA
<213> ORGANISM: Artificial Sequence
<220> FEATURE:
<223> OTHER INFORMATION: ADV-28
<220> FEATURE:
<221> NAME/KEY: misc_feature
<222> LOCATION: (12)..(12)
<223> OTHER INFORMATION: n is dI
<220> FEATURE:
<221> NAME/KEY: misc_feature
<222> LOCATION: (17)..(17)
<223> OTHER INFORMATION: n is dI

<400> SEQUENCE: 23
ggcccgagat gngcatnta                                              19

<210> SEQ ID NO 24
<211> LENGTH: 19
<212> TYPE: DNA
<213> ORGANISM: Artificial Sequence
<220> FEATURE:
<223> OTHER INFORMATION: ADV-13 primer
<220> FEATURE:
<221> NAME/KEY: misc_feature
<222> LOCATION: (12)..(12)
<223> OTHER INFORMATION: n is I04
<220> FEATURE:
```

```
<221> NAME/KEY: misc_feature
<222> LOCATION: (14)..(14)
<223> OTHER INFORMATION: n is I04

<400> SEQUENCE: 24
ggcccgagat gngnatgta                                               19

<210> SEQ ID NO 25
<211> LENGTH: 19
<212> TYPE: DNA
<213> ORGANISM: Artificial Sequence
<220> FEATURE:
<223> OTHER INFORMATION: ADV-14 primer
<220> FEATURE:
<221> NAME/KEY: misc_feature
<222> LOCATION: (12)..(12)
<223> OTHER INFORMATION: n is I04
<220> FEATURE:
<221> NAME/KEY: misc_feature
<222> LOCATION: (15)..(15)
<223> OTHER INFORMATION: n is I04

<400> SEQUENCE: 25
ggcccgagat gngcntgta                                               19

<210> SEQ ID NO 26
<211> LENGTH: 19
<212> TYPE: DNA
<213> ORGANISM: Artificial Sequence
<220> FEATURE:
<223> OTHER INFORMATION: ADV-15 primer
<220> FEATURE:
<221> NAME/KEY: misc_feature
<222> LOCATION: (12)..(12)
<223> OTHER INFORMATION: n is I04
<220> FEATURE:
<221> NAME/KEY: misc_feature
<222> LOCATION: (16)..(16)
<223> OTHER INFORMATION: n is I04

<400> SEQUENCE: 26
ggcccgagat gngcangta                                               19

<210> SEQ ID NO 27
<211> LENGTH: 19
<212> TYPE: DNA
<213> ORGANISM: Artificial Sequence
<220> FEATURE:
<223> OTHER INFORMATION: ADV-16 primer
<220> FEATURE:
<221> NAME/KEY: misc_feature
<222> LOCATION: (12)..(12)
<223> OTHER INFORMATION: n is I04
<220> FEATURE:
<221> NAME/KEY: misc_feature
<222> LOCATION: (16)..(16)
<223> OTHER INFORMATION: n is I04
<220> FEATURE:
<221> NAME/KEY: misc_feature
<222> LOCATION: (17)..(17)
<223> OTHER INFORMATION: n is I04

<400> SEQUENCE: 27
ggcccgagat gngcatnta                                               19

<210> SEQ ID NO 28
<211> LENGTH: 19
<212> TYPE: DNA
<213> ORGANISM: Artificial Sequence
<220> FEATURE:
<223> OTHER INFORMATION: ADV-17 primer
```

```
<220> FEATURE:
<221> NAME/KEY: misc_feature
<222> LOCATION: (12)..(12)
<223> OTHER INFORMATION: n is I07
<220> FEATURE:
<221> NAME/KEY: misc_feature
<222> LOCATION: (14)..(14)
<223> OTHER INFORMATION: n is I07

<400> SEQUENCE: 28
ggcccgagat gngnatgta                                                19

<210> SEQ ID NO 29
<211> LENGTH: 19
<212> TYPE: DNA
<213> ORGANISM: Artificial Sequence
<220> FEATURE:
<223> OTHER INFORMATION: ADV-18
<220> FEATURE:
<221> NAME/KEY: misc_feature
<222> LOCATION: (12)..(12)
<223> OTHER INFORMATION: n is I07
<220> FEATURE:
<221> NAME/KEY: misc_feature
<222> LOCATION: (15)..(15)
<223> OTHER INFORMATION: n is I07

<400> SEQUENCE: 29
ggcccgagat gngcntgta                                                19

<210> SEQ ID NO 30
<211> LENGTH: 19
<212> TYPE: DNA
<213> ORGANISM: Artificial Sequence
<220> FEATURE:
<223> OTHER INFORMATION: ADV-19 primer
<220> FEATURE:
<221> NAME/KEY: misc_feature
<222> LOCATION: (12)..(12)
<223> OTHER INFORMATION: n is I07
<220> FEATURE:
<221> NAME/KEY: misc_feature
<222> LOCATION: (16)..(16)
<223> OTHER INFORMATION: n is I07

<400> SEQUENCE: 30
ggcccgagat gngcangta                                                19

<210> SEQ ID NO 31
<211> LENGTH: 19
<212> TYPE: DNA
<213> ORGANISM: Artificial Sequence
<220> FEATURE:
<223> OTHER INFORMATION: ADV-20
<220> FEATURE:
<221> NAME/KEY: misc_feature
<222> LOCATION: (12)..(12)
<223> OTHER INFORMATION: n is I07
<220> FEATURE:
<221> NAME/KEY: misc_feature
<222> LOCATION: (17)..(17)
<223> OTHER INFORMATION: n is I07

<400> SEQUENCE: 31
ggcccgagat gngcatnta                                                19

<210> SEQ ID NO 32
<211> LENGTH: 19
<212> TYPE: DNA
<213> ORGANISM: Artificial Sequence
<220> FEATURE:
```

```
<223> OTHER INFORMATION: ADV-29 primer
<220> FEATURE:
<221> NAME/KEY: misc_feature
<222> LOCATION: (18)..(18)
<223> OTHER INFORMATION: n is dI

<400> SEQUENCE: 32
ggcccgagat gtgcatgna                                               19

<210> SEQ ID NO 33
<211> LENGTH: 19
<212> TYPE: DNA
<213> ORGANISM: Artificial Sequence
<220> FEATURE:
<223> OTHER INFORMATION: ADV-30 primer
<220> FEATURE:
<221> NAME/KEY: misc_feature
<222> LOCATION: (19)..(19)
<223> OTHER INFORMATION: n is dI

<400> SEQUENCE: 33
ggcccgagat gtgcatgtn                                               19

<210> SEQ ID NO 34
<211> LENGTH: 19
<212> TYPE: DNA
<213> ORGANISM: Artificial Sequence
<220> FEATURE:
<223> OTHER INFORMATION: ADV-21
<220> FEATURE:
<221> NAME/KEY: misc_feature
<222> LOCATION: (18)..(18)
<223> OTHER INFORMATION: n is I04

<400> SEQUENCE: 34
ggcccgagat gtgcatgna                                               19

<210> SEQ ID NO 35
<211> LENGTH: 19
<212> TYPE: DNA
<213> ORGANISM: Artificial Sequence
<220> FEATURE:
<223> OTHER INFORMATION: ADV-22 primer
<220> FEATURE:
<221> NAME/KEY: misc_feature
<222> LOCATION: (19)..(19)
<223> OTHER INFORMATION: n is I04

<400> SEQUENCE: 35
ggcccgagat gtgcatgtn                                               19

<210> SEQ ID NO 36
<211> LENGTH: 19
<212> TYPE: DNA
<213> ORGANISM: Artificial Sequence
<220> FEATURE:
<223> OTHER INFORMATION: ADV-23 primer
<220> FEATURE:
<221> NAME/KEY: misc_feature
<222> LOCATION: (18)..(18)
<223> OTHER INFORMATION: n is I07

<400> SEQUENCE: 36
ggcccgagat gtgcatgna                                               19

<210> SEQ ID NO 37
<211> LENGTH: 19
<212> TYPE: DNA
<213> ORGANISM: Artificial Sequence
```

```
<220> FEATURE:
<223> OTHER INFORMATION: ADV-24 primer
<220> FEATURE:
<221> NAME/KEY: misc_feature
<222> LOCATION: (19)..(19)
<223> OTHER INFORMATION: n is I07

<400> SEQUENCE: 37
ggcccgagat gtgcatgtn                                                          19

<210> SEQ ID NO 38
<211> LENGTH: 19
<212> TYPE: DNA
<213> ORGANISM: Artificial Sequence
<220> FEATURE:
<223> OTHER INFORMATION: ADV-32 primer
<220> FEATURE:
<221> NAME/KEY: misc_feature
<222> LOCATION: (9)..(9)
<223> OTHER INFORMATION: n is dI
<220> FEATURE:
<221> NAME/KEY: misc_feature
<222> LOCATION: (12)..(12)
<223> OTHER INFORMATION: n is dI
<220> FEATURE:
<221> NAME/KEY: misc_feature
<222> LOCATION: (15)..(15)
<223> OTHER INFORMATION: n is dI

<400> SEQUENCE: 38
ggcccgagnt gngcntgta                                                          19

<210> SEQ ID NO 39
<211> LENGTH: 19
<212> TYPE: DNA
<213> ORGANISM: Artificial Sequence
<220> FEATURE:
<223> OTHER INFORMATION: ADV-31 primer
<220> FEATURE:
<221> NAME/KEY: misc_feature
<222> LOCATION: (10)..(10)
<223> OTHER INFORMATION: n is dI
<220> FEATURE:
<221> NAME/KEY: misc_feature
<222> LOCATION: (12)..(12)
<223> OTHER INFORMATION: n is dI
<220> FEATURE:
<221> NAME/KEY: misc_feature
<222> LOCATION: (15)..(15)
<223> OTHER INFORMATION: n is dI

<400> SEQUENCE: 39
ggcccgagan gngcntgta                                                          19

<210> SEQ ID NO 40
<211> LENGTH: 19
<212> TYPE: DNA
<213> ORGANISM: Artificial Sequence
<220> FEATURE:
<223> OTHER INFORMATION: ADV-34 primer
<220> FEATURE:
<221> NAME/KEY: misc_feature
<222> LOCATION: (9)..(9)
<223> OTHER INFORMATION: n is I04
<220> FEATURE:
<221> NAME/KEY: misc_feature
<222> LOCATION: (12)..(12)
<223> OTHER INFORMATION: n is I04
<220> FEATURE:
<221> NAME/KEY: misc_feature
<222> LOCATION: (15)..(15)
<223> OTHER INFORMATION: n is I04
```

-continued

```
<400> SEQUENCE: 40
ggcccgagnt gngcntgta                                                19

<210> SEQ ID NO 41
<211> LENGTH: 19
<212> TYPE: DNA
<213> ORGANISM: Artificial Sequence
<220> FEATURE:
<223> OTHER INFORMATION: ADV-33 primer
<220> FEATURE:
<221> NAME/KEY: misc_feature
<222> LOCATION: (10)..(10)
<223> OTHER INFORMATION: n is I04
<220> FEATURE:
<221> NAME/KEY: misc_feature
<222> LOCATION: (12)..(12)
<223> OTHER INFORMATION: n is I04
<220> FEATURE:
<221> NAME/KEY: misc_feature
<222> LOCATION: (15)..(15)
<223> OTHER INFORMATION: n is I04

<400> SEQUENCE: 41
ggcccgagan gngcntgta                                                19

<210> SEQ ID NO 42
<211> LENGTH: 19
<212> TYPE: DNA
<213> ORGANISM: Artificial Sequence
<220> FEATURE:
<223> OTHER INFORMATION: ADV-36 primer
<220> FEATURE:
<221> NAME/KEY: misc_feature
<222> LOCATION: (9)..(9)
<223> OTHER INFORMATION: n is I07
<220> FEATURE:
<221> NAME/KEY: misc_feature
<222> LOCATION: (12)..(12)
<223> OTHER INFORMATION: n is I07
<220> FEATURE:
<221> NAME/KEY: misc_feature
<222> LOCATION: (15)..(15)
<223> OTHER INFORMATION: n is I07

<400> SEQUENCE: 42
ggcccgagnt gngcntgta                                                19

<210> SEQ ID NO 43
<211> LENGTH: 19
<212> TYPE: DNA
<213> ORGANISM: Artificial Sequence
<220> FEATURE:
<223> OTHER INFORMATION: ADV-35 primer
<220> FEATURE:
<221> NAME/KEY: misc_feature
<222> LOCATION: (10)..(10)
<223> OTHER INFORMATION: n is I07
<220> FEATURE:
<221> NAME/KEY: misc_feature
<222> LOCATION: (12)..(12)
<223> OTHER INFORMATION: n is I07
<220> FEATURE:
<221> NAME/KEY: misc_feature
<222> LOCATION: (15)..(15)
<223> OTHER INFORMATION: n is I07

<400> SEQUENCE: 43
ggcccgagan gngcntgta                                                19

<210> SEQ ID NO 44
<211> LENGTH: 28
```

```
<212> TYPE: DNA
<213> ORGANISM: Artificial Sequence
<220> FEATURE:
<223> OTHER INFORMATION: LGA-L23

<400> SEQUENCE: 44
gtatatttcc gttattttct aaagcact                                              28

<210> SEQ ID NO 45
<211> LENGTH: 28
<212> TYPE: DNA
<213> ORGANISM: Artificial Sequence
<220> FEATURE:
<223> OTHER INFORMATION: LGA-L24
<220> FEATURE:
<221> NAME/KEY: misc_feature
<222> LOCATION: (6)..(6)
<223> OTHER INFORMATION: n is dI
<220> FEATURE:
<221> NAME/KEY: misc_feature
<222> LOCATION: (15)..(15)
<223> OTHER INFORMATION: n is dI
<220> FEATURE:
<221> NAME/KEY: misc_feature
<222> LOCATION: (18)..(18)
<223> OTHER INFORMATION: n is dI
<220> FEATURE:
<221> NAME/KEY: misc_feature
<222> LOCATION: (21)..(21)
<223> OTHER INFORMATION: n is dI
<220> FEATURE:
<221> NAME/KEY: misc_feature
<222> LOCATION: (23)..(23)
<223> OTHER INFORMATION: n is dI

<400> SEQUENCE: 45
gtatanttcc gttanttnct nangcact                                              28

<210> SEQ ID NO 46
<211> LENGTH: 29
<212> TYPE: DNA
<213> ORGANISM: Artificial Sequence
<220> FEATURE:
<223> OTHER INFORMATION: LGA-L25
<220> FEATURE:
<221> NAME/KEY: misc_feature
<222> LOCATION: (6)..(6)
<223> OTHER INFORMATION: n is I07
<220> FEATURE:
<221> NAME/KEY: misc_feature
<222> LOCATION: (15)..(15)
<223> OTHER INFORMATION: n is I07
<220> FEATURE:
<221> NAME/KEY: misc_feature
<222> LOCATION: (18)..(18)
<223> OTHER INFORMATION: n is I07
<220> FEATURE:
<221> NAME/KEY: misc_feature
<222> LOCATION: (21)..(21)
<223> OTHER INFORMATION: n is I07
<220> FEATURE:
<221> NAME/KEY: misc_feature
<222> LOCATION: (23)..(23)
<223> OTHER INFORMATION: n is I07

<400> SEQUENCE: 46
gtatanttcc gttanttnct nangcactg                                             29

<210> SEQ ID NO 47
<211> LENGTH: 37
<212> TYPE: DNA
<213> ORGANISM: Artificial Sequence
<220> FEATURE:
```

<223> OTHER INFORMATION: LGA-E3

<400> SEQUENCE: 47
aataaatcat aaggccaagg cgagatacta gtaaacc            37

<210> SEQ ID NO 48
<211> LENGTH: 17
<212> TYPE: DNA
<213> ORGANISM: Artificial Sequence
<220> FEATURE:
<223> OTHER INFORMATION: LGA-FAM5
<220> FEATURE:
<221> NAME/KEY: misc_feature
<222> LOCATION: (1)..(1)
<223> OTHER INFORMATION: n is Super G conjugated to FAM and minor groove
      binder (MGB)
<220> FEATURE:
<221> NAME/KEY: misc_feature
<222> LOCATION: (6)..(6)
<223> OTHER INFORMATION: n is Super A
<220> FEATURE:
<221> NAME/KEY: misc_feature
<222> LOCATION: (8)..(8)
<223> OTHER INFORMATION: n is Super T
<220> FEATURE:
<221> NAME/KEY: misc_feature
<222> LOCATION: (9)..(9)
<223> OTHER INFORMATION: n is Super T
<220> FEATURE:
<221> NAME/KEY: misc_feature
<222> LOCATION: (10)..(10)
<223> OTHER INFORMATION: n is Super T
<220> FEATURE:
<221> NAME/KEY: misc_feature
<222> LOCATION: (13)..(13)
<223> OTHER INFORMATION: n is Super A
<220> FEATURE:
<221> NAME/KEY: misc_feature
<222> LOCATION: (15)..(15)
<223> OTHER INFORMATION: n is Super A
<220> FEATURE:
<221> NAME/KEY: misc_feature
<222> LOCATION: (17)..(17)
<223> OTHER INFORMATION: n is G conjugated to Eclipse Dark Quencher
      (EDQ)

<400> SEQUENCE: 48
nataanannn gtntngn            17

<210> SEQ ID NO 49
<211> LENGTH: 23
<212> TYPE: DNA
<213> ORGANISM: Artificial Sequence
<220> FEATURE:
<223> OTHER INFORMATION: Complement

<400> SEQUENCE: 49
aaagttatgt ctacttacag aaa            23

<210> SEQ ID NO 50
<211> LENGTH: 23
<212> TYPE: DNA
<213> ORGANISM: Artificial Sequence
<220> FEATURE:
<223> OTHER INFORMATION: Complement

<400> SEQUENCE: 50
aaagttatgt cttcttacag aaa            23

<210> SEQ ID NO 51
<211> LENGTH: 23

```
<212> TYPE: DNA
<213> ORGANISM: Artificial Sequence
<220> FEATURE:
<223> OTHER INFORMATION: Complement

<400> SEQUENCE: 51
aaagttatgt ctccttacag aaa                                              23

<210> SEQ ID NO 52
<211> LENGTH: 23
<212> TYPE: DNA
<213> ORGANISM: Artificial Sequence
<220> FEATURE:
<223> OTHER INFORMATION: Complement

<400> SEQUENCE: 52
aaagttatgt ctgcttacag aaa                                              23

<210> SEQ ID NO 53
<211> LENGTH: 23
<212> TYPE: DNA
<213> ORGANISM: Artificial Sequence
<220> FEATURE:
<223> OTHER INFORMATION: Complement

<400> SEQUENCE: 53
aaagttatga ctacttacag aaa                                              23

<210> SEQ ID NO 54
<211> LENGTH: 23
<212> TYPE: DNA
<213> ORGANISM: Artificial Sequence
<220> FEATURE:
<223> OTHER INFORMATION: Complement

<400> SEQUENCE: 54
aaagttatgc ctacttacag aaa                                              23

<210> SEQ ID NO 55
<211> LENGTH: 23
<212> TYPE: DNA
<213> ORGANISM: Artificial Sequence
<220> FEATURE:
<223> OTHER INFORMATION: Complement

<400> SEQUENCE: 55
aaagttatgg ctacttacag aaa                                              23

<210> SEQ ID NO 56
<211> LENGTH: 23
<212> TYPE: DNA
<213> ORGANISM: Artificial Sequence
<220> FEATURE:
<223> OTHER INFORMATION: Complement

<400> SEQUENCE: 56
aaagttatga cttcttacag aaa                                              23

<210> SEQ ID NO 57
<211> LENGTH: 23
<212> TYPE: DNA
<213> ORGANISM: Artificial Sequence
<220> FEATURE:
<223> OTHER INFORMATION: Complement

<400> SEQUENCE: 57
```
aaagttatgc cttcttacag aaa                                                  23

<210> SEQ ID NO 58
<211> LENGTH: 23
<212> TYPE: DNA
<213> ORGANISM: Artificial Sequence
<220> FEATURE:
<223> OTHER INFORMATION: Complement

<400> SEQUENCE: 58
aaagttatgg cttcttacag aaa                                                  23

<210> SEQ ID NO 59
<211> LENGTH: 23
<212> TYPE: DNA
<213> ORGANISM: Artificial Sequence
<220> FEATURE:
<223> OTHER INFORMATION: Complement

<400> SEQUENCE: 59
aaagttatga ctccttacag aaa                                                  23

<210> SEQ ID NO 60
<211> LENGTH: 23
<212> TYPE: DNA
<213> ORGANISM: Artificial Sequence
<220> FEATURE:
<223> OTHER INFORMATION: Complement

<400> SEQUENCE: 60
aaagttatgc ctccttacag aaa                                                  23

<210> SEQ ID NO 61
<211> LENGTH: 23
<212> TYPE: DNA
<213> ORGANISM: Artificial Sequence
<220> FEATURE:
<223> OTHER INFORMATION: Complement

<400> SEQUENCE: 61
aaagttatgg ctccttacag aaa                                                  23

<210> SEQ ID NO 62
<211> LENGTH: 23
<212> TYPE: DNA
<213> ORGANISM: Artificial Sequence
<220> FEATURE:
<223> OTHER INFORMATION: Complement

<400> SEQUENCE: 62
aaagttatga ctgcttacag aaa                                                  23

<210> SEQ ID NO 63
<211> LENGTH: 23
<212> TYPE: DNA
<213> ORGANISM: Artificial Sequence
<220> FEATURE:
<223> OTHER INFORMATION: Complement

<400> SEQUENCE: 63
aaagttatgc ctgcttacag aaa                                                  23

<210> SEQ ID NO 64
<211> LENGTH: 23
<212> TYPE: DNA
<213> ORGANISM: Artificial Sequence -continued
<220> FEATURE:
<223> OTHER INFORMATION: Complement

<400> SEQUENCE: 64
aaagttatgg ctgcttacag aaa                                              23

<210> SEQ ID NO 65
<211> LENGTH: 91
<212> TYPE: DNA
<213> ORGANISM: Artificial Sequence
<220> FEATURE:
<223> OTHER INFORMATION: Target

<400> SEQUENCE: 65
acatgaggat tttgtatatt tccgttattt tctaaagcac tgtatattga taaaatttgt      60
atagggttta ctagtatctc gccttggcca t                                     91

<210> SEQ ID NO 66
<211> LENGTH: 38
<212> TYPE: DNA
<213> ORGANISM: Artificial Sequence
<220> FEATURE:
<223> OTHER INFORMATION: Natural F primer

<400> SEQUENCE: 66
gaggattttg tatatttccg ttattttcta aagcactg                              38

<210> SEQ ID NO 67
<211> LENGTH: 38
<212> TYPE: DNA
<213> ORGANISM: Artificial Sequence
<220> FEATURE:
<223> OTHER INFORMATION: F(I01) Primer
<220> FEATURE:
<221> NAME/KEY: misc_feature
<222> LOCATION: (24)..(24)
<223> OTHER INFORMATION: n is I01
<220> FEATURE:
<221> NAME/KEY: misc_feature
<222> LOCATION: (27)..(27)
<223> OTHER INFORMATION: n is I01

<400> SEQUENCE: 67
gaggattttg tatatttccg ttanttncta aagcactg                              38

<210> SEQ ID NO 68
<211> LENGTH: 38
<212> TYPE: DNA
<213> ORGANISM: Artificial Sequence
<220> FEATURE:
<223> OTHER INFORMATION: F(I07) Primer
<220> FEATURE:
<221> NAME/KEY: misc_feature
<222> LOCATION: (24)..(24)
<223> OTHER INFORMATION: n is I07
<220> FEATURE:
<221> NAME/KEY: misc_feature
<222> LOCATION: (27)..(27)
<223> OTHER INFORMATION: n is I07

<400> SEQUENCE: 68
gaggattttg tatatttccg ttanttncta aagcactg                              38

<210> SEQ ID NO 69
<211> LENGTH: 38
<212> TYPE: DNA
<213> ORGANISM: Artificial Sequence
<220> FEATURE:

```
<223> OTHER INFORMATION: Natural F Primer reverse strand

<400> SEQUENCE: 69
cagtgcttta gaaaataacg gaaatataca aaatcctc                                38

<210> SEQ ID NO 70
<211> LENGTH: 38
<212> TYPE: DNA
<213> ORGANISM: Artificial Sequence
<220> FEATURE:
<223> OTHER INFORMATION: Amplicon complementary to F(dI) Primer
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t

<400> SEQUENCE: 70
cagngcttta gcaactaacg gaaatataca aaannctc                                38

<210> SEQ ID NO 71
<211> LENGTH: 38
<212> TYPE: DNA
<213> ORGANISM: Artificial Sequence
<220> FEATURE:
<223> OTHER INFORMATION: Amplicon complementary to F(I07) Primer
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t

<400> SEQUENCE: 71 cannnctta gcaactaacg gaaanataca aaatcctn                                 38
```

FUNCTIONALIZED 3-ALKYNYL PYRAZOLOPYRIMIDINE ANALOGUES AS UNIVERSAL BASES AND METHODS OF USE

This application claims priority to U.S. Provisional Patent Application Ser. No. 61/466,755, entitled "FUNCTIONALIZED 3-ALKYNYL INOSINE ANALOGUES AS UNIVERSAL BASES AND METHODS OF USE," filed on Mar. 23, 2011, the entire content of which is hereby incorporated by reference.

BACKGROUND

This invention relates to universal bases and their uses.

Universal bases are extensively used in primers, probes, hybridization, sequencing, cloning and the diagnostic detection of infectious targets. A universal base analogue forms base pairs with each of the natural bases with little discrimination between them (Loakes et al., 1997; Loakes, 2001). Desirable requirements for a universal base include the ability to: a) pair with all natural bases equally in a duplex, b) form a duplex which primes DNA synthesis by a polymerase, c) direct incorporation of the 5'-triphosphate of each of the natural nucleosides opposite it when copied by a polymerase, (d) be a substrate for polymerases as the 5"-triphosphate, e) be recognized by intracellular enzymes such that DNA containing them may be cloned. (Loakes et al. 1997). At present no analogue has been shown to have all these characteristics.

Hypoxanthine functions as a universal pairing base (Graig, 1966). Nearest-neighbor thermodynamics of 2"-deoxyinosine (2-deoxy-β-D-ribofuranosyl-hypoxanthine) pairs in DNA duplexes have been reported (Watkins and SantaLucia, 2005). The general trend in stability was reported as I:C>I:A>I:T≈I:G>I:I. 2'-Deoxyinosine has found use as a universal nucleoside and is far less non-discriminating than nitroazole derivatives (Bergstrom et al, 1997). $T_m$ values vary from 35.4° C. when paired with G to 63.2° C. when paired with C. A universal 2"-deoxyinosine analogue 7-octadiynyl-7-deaza-7-deox) inosine has also been disclosed (Ming et al. 2008). The nucleobase of this analogue shows universal binding properties with the four natural bases in a 12-mer oligonucleotide with $T_m$'s that varies from 45° C. for C to 34° C. for G.

Destabilization of a duplex when a natural base is substituted with a universal base is a relatively common occurrence and one of the weaknesses of most universal bases in the art.

SUMMARY

The present disclosure pertains to functionalized 3-alkynyl-1H-pyrazolo[3,4-d]pyrimidin-4(5H)-ones as universal bases and their methods of use.

3-alkynyl-1H-pyrazolo[3,4-d]pyrimidin-4(5H)-one-based analogues function unexpectedly well as universal bases. Not only do they stabilize duplexes substantially more than hypoxanthine opposite A, C, and T but they are also recognized in primers by polymerases, allowing efficient amplification. 1H-Pyrazolo[3,4-d]pyrimidin-4(5H)-ones substituted at the 3-position with hydroxylalkynyl (IPPOH) or aminoalkynyl (IPPNH$_2$) are preferred as universal bases.

Nucleosides containing functionalized 3-alkynyl-1H-pyrazolo[3,4-d]pyrimidine-4-ones structures have been disclosed in U.S. Pat. No. 7,045,610, incorporated herein by reference, but no hybridization characteristics of oligonucleotides containing these bases or direct synthetic methods were disclosed.

The 3-alkynyl-1H-pyrazolo[3,4-d]pyrimidin-4(5H)-one analogues can be incorporated into novel nucleic acid primers and probes. They do not significantly destabilize nucleic acid duplexes, as other universal bases do. As a result, the novel nucleic acid primers and probes incorporating the 3-alkynyl-1H-pyrazolo[3,4-d]pyrimidin-4(5H)-one analogues can be used in a variety of methods.

BRIEF DESCRIPTION OF DRAWINGS

FIG. 10 shows a summary of melting temperatures ($T_m$s) of duplexes between the 15-mer GTAAGXAGXCATAAC (SEQ ID NO:1), the 15-mer GTAAGXAGACATAAC (SEQ ID NO:2), and the 15-mer GTAAGTAGXCATAAC (SEQ ID NO:3), where X is independently 2'-deoxinosine or a 2-deoxy-β-D-ribofuranosyl-3-alkynyl-1H-pyrazolo[3,4-d]pyrimidin-4(5H)-one of the present disclosure, and the complement which contains either A, T, C or G opposite to X.

FIG. 14 shows a comparison of melting and real-time PCR data for Adenovirus assays using primers containing the currently described nucleoside analogues.

FIG. 15 shows a comparison of melting and real-time PCR data for Adenovirus assays using primers containing multiple incorporations of the currently described nucleoside analogues.

FIG. 16 shows a comparison of Cts for a Meticillin-resistant *Staphylococcus aureus* LGA251 target assay using primers substituted with five deoxyinosine or five 3-(aminobutynyl)-1h-pyrazolo[3,4-d]pyrimidin-4(5h)-one nucleotides.

FIG. 17 shows that when two Ts in a primer are substituted with either deoxy inosine or 3-(aminobutynyl)-1h-pyrazolo [3,4-d]pyrimidin-4(5h)-one nucleotides that the polymerase incorporate two Cs complementary to the Ts.

DETAILED DESCRIPTION

I. Definitions

Figure 1:
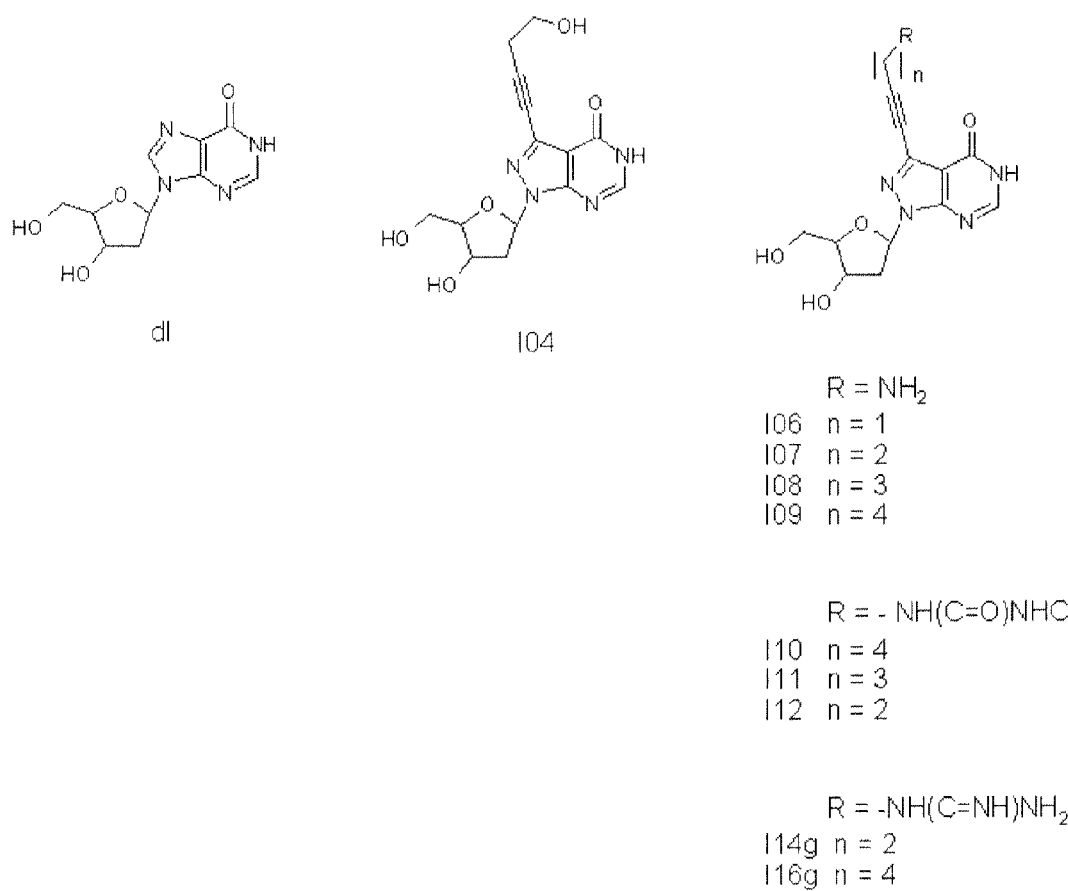
FIG. 1 shows the structure of 2'-deoxyinosine and 2-deoxy-β-D-ribofuranosyl-3-substituted-1H-pyrazolo[3,4-d]pyrimidin-4(5H)-ones.

Unless stated otherwise, the following terms and phrases have the meanings provided below:

The term "target sequence" refers to a sequence in a target RNA, or DNA that is partially or fully complementary to the mature strand. The target sequence can be described using the four bases of DNA (A, T, G, and C), or the four bases of RNA (A, U, G, and C).

The term "complementary" refers to the ability of polynucleotides to form base pairs with one another. Base pairs are typically formed by hydrogen bonds between nucleotide units in antiparallel polynucleotide strands. Complementary polynucleotide strands can base pair in the Watson-Crick manner (e.g., A to T, A to U, C to G), or in any other manner that allows for the formation of duplexes, including the wobble base pair formed between U and G. As persons skilled in the art are aware, when using RNA as opposed to DNA, uracil rather than thymine is the base that is considered to be complementary to adenosine. However, when a U is denoted in the context of the present invention, the ability to substitute a T is implied, unless otherwise stated. The inosine modified bases of the pending application hybridize with similar stabilities than those of normal base pairs. It is therefore viewed that the term "complementary" includes hybridization of the functionalized 3-alkynyl-1H-pyrazolo[3,4-d]pyrimidin-4 (5H)-ones as universal bases to A, C, T or G.

The term "substantially" complementary refers to the ability of an oligonucleotide to form base pairs specifically with another oligonucleotide where said oligonucleotide may contain one or more mismatches.

The term "duplex" refers to a double stranded structure formed by two complementary or substantially complementary polynucleotides that form base pairs with one another, including Watson-Crick base pairs and U-G wobble pairs that allow for a stabilized double stranded structure between poly nucleotide strands that are at least partially complementary. The strands of a duplex need not be perfectly complementary for a duplex to form, i.e., a duplex may include one or more base mismatches. In addition, duplexes can be formed between two complementary regions within a single strand (e.g., a hairpin).

The term "nucleotide" refers to a ribonucleotide or a deoxyribonucleotide or modified form thereof as well as an analog thereof. Nucleotides include species that comprise purines, e.g., adenine, hypoxanthine, guanine, and their derivatives and analogues, as well as pyrimidines, e.g., cytosine, uracil, thymine, and their derivatives and analogues. Nucleotide analogues include nucleotides having modifications in the chemical structure of the base, sugar and/or phosphate, including, but not limited to, 5-position pyrimidine modifications, 8-position purine modifications, modifications at cytosine exocyclic amines, and substitution of 5-bromouracil; and 2'-position sugar modifications, including but not limited to, sugar-modified ribonucleotides in which the 2'-OH is replaced by a group such as an H, OR, R, halo, SH, SR, $NH_2$, NHR, $NR_2$, or CN, wherein R is an alkyl moiety. Nucleotide analogues are also meant to include nucleotides with bases such as inosine, queuosine, xanthine, sugars such as 2'-methyl ribose, non-natural phosphodiester linkages such as in ethylphosphonates, phosphorothioates and peptides.

The term "modified bases" refers to those bases that differ from the naturally-occurring bases (adenine, cytosine, guanine, thymine, and urasil) by addition or deletion of one or more functional groups, differences in the heterocyclic ring structure (i.e., substitution of carbon for a heteroatom, or vice versa), and/or attachment of one or more linker arm structures to the base. Preferred modified nucleotides are those based on a pyrimidine structure or a purine structure, with the latter more preferably being 7 deazapurines and their derivatives and pyrazolopyrimidines (described in PCT WO 01/84958); and also described in U.S. Pat. No. 6,127,121. Preferred modified bases are 5-substituted pyrimidines and 3-substituted pyrazolopyrimidines. Examples of preferred modified bases are 6-amino-1H-pyrazolo[3,4-d]pyrimidin-4(5H)-one (PPG or Super G®), 4-amino-1H-pyrazolo[3,4-d]pyrimidine, 1H-pyrazolo[5,4-d]pyrimidin-4(5H)-6(7H)-dione, 6-amino-3-prop-1-ynyl-5-hydropyrazolo[3,4-d]pyrimidine-4-one, 6-amino-3-(3-hydroxyprop-1-ynyl)-5-hydropyrazolo [3,4-d]pyrimidine-4-one. 6-amino-3-(3-aminoprop-1-ynyl)-5-hydropyrazolo[3,4-d]pyrimidine-4-one. 4-amino-3-(prop-1-ynyl)pyrazolo[3,4-d]pyrimidine. 4-amino-3-(3-hydroxyprop-1-ynyl)pyrazolo[3,4-d]pyrimidine. 4-amino-3-(3-aminoprop-1-ynyl)pyrazolo[3,4-d]pyrimidine. 3-prop-1-ynyl-4,6-diaminopyrazolo[3,4-d]pyrimidine, 2-(4,6-diaminopyrazolo[3,4-d]pyrimidin-3-yl)ethynyl-1-ol, 3-(2-aminoethynyl)pyrazolo[3,4-d]pyrimidine-4,6-diamine, 5-prop-1-ynyl-1,3-dihydropyrimidine-2,4-dione, 5-(3-hydroxyprop-1-ynyl)-1,3-dihydropyrimidine-2,4-dione, 6-amino-5-prop-1-ynyl-3-dihydropyrimidine-2-one, 6-amino-5-(3-hydroxyprop-1-yny)-1,3-dihydropyrimidine-2-one, 6-amino-5-(3-aminoprop-1-yny)-1,3-dihydropyrimidine-2-one, 5-[4-amino-3-(3-methoxyprop-1-ynyl)pyrazol [3,4-d]pyrimidinyl]-2-(hydroxymethyl)oxolan-3-ol, 6-amino-1-[4-hydroxy-5-(hydroxymethyl)oxolan-2-yl]-3-(3-methoxyprop-1-ynyl)-5-hydropyrazolo[3,4-d]pyrimidin-4-one, 4-(4,6-Diamino-1,1-pyrazolo[3,4-d]pyrimidin-3-yl)-but-3-yn-1-ol (Super A 6-Amino-3-(4-hydroxy-but-1-ynyl)-1,5-dihydro-pyrazolo[3,4-d]pyrimidin-4-one, 5-(4-hydroxybut-1-ynyl)-1H-pyrimidine-2,4-dione (Super T), 3-iodo-1H-pyrazolo[3,4-d]pyrimidine-4,6-diamine, 3-bromo-1H-pyrazolo[3,4-d]pyrimidine-4,6-diamine, 3-chloro-1H-pyrazolo[3,4-d]pyrimidine-4,6-diamine, 3-Iodo-1H-pyrazolo[3,4-d]pyrimidin-4-ylamine, 3-Bromo-1H-pyrazolo [3,4-d]pyrimidin-4-ylamine and 3-chloro-1H-pyrazolo[3,4-d]pyrimidin-4-ylamine.

The terms "universal bases" and "degenerative bases" refer to natural base analogues that are capable of forming base pairs with two or more natural bases in DNA or RNA with little discrimination between them. Universal and degenerative bases are well known in the art and disclosed in U.S. Pat. No. 7,348,146 that is incorporated by reference. Oligonucleotide conjugates containing an inosine analog of the current disclosure may also comprise one or more universal and degenerative bases, in addition to the naturally-occurring bases adenine, cytosine, guanine, thymine and uracil.

The term "nucleotide" is also meant to include what are known in the art as universal bases. By way of example, universal bases include, but are not limited to, 3-nitropyrrole, 5-nitroindole, or nebularine. The term "nucleotide" is also meant to include the N3' to P5' phosphoramidate, resulting from the substitution of a ribosyl 3'-oxygen with an amine group. Further, the term nucleotide also includes those species that have a detectable label, such as for example a radioactive or fluorescent moiety, or mass label attached to the nucleotide.

The term "linker" refers to a moiety that is used to assemble various portions of the molecule or to covalently attach the molecule (or portions thereof) to a solid support. Additionally, a linker can include linear or acyclic portions, cyclic portions, aromatic rings or combinations thereof.

The term "protecting group" refers to a grouping of atoms that when attached to a reactive group in a molecule masks, reduces or prevents that reactivity. Examples of protecting groups can be found in T. W. Greene and P. G. Futs. Protective Groups in Organic Chemistry, (Wiley, 2nd ed. 1991). Beaucage and Iyer, Tetrahedron 48:2223-2311 (1992), and Harrison and Harrison et al., Compendium of Synthetic Organic Methods, Vols. 1-8 (John Wiley and Sons. 1971-1996). Representative amino protecting groups include formyl, acetyl, trifluoroacetyl, benzyl, benzyloxy carbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC) and the like. Representative hydroxy protecting groups include those where the hydroxy group is either acylated or alkylated such as benzyl and trityl ethers as well as alkyl ethers, tetrahydropyranyl ethers, trialkylsilyl ethers and allyl ethers. These protecting groups can be removed under conditions which are compatible with the integrity of a compound of interest. Deprotection conditions are well known in the art and described in the references above.

The term "alkyl" refers to a linear, branched, or cyclic saturated monovalent hydrocarbon radical or a combination of cyclic and linear or branched saturated monovalent hydrocarbon radicals having the number of carbon atoms indicated in the prefix. For example, $(C_1-C_8)$alkyl is meant to include methyl, ethyl, n-propyl, 2-propyl, tert-butyl, pentyl, cyclopentyl, cyclopropylmethyl and the like.

There is extensive guidance in the art for selecting quencher and fluorophore pairs and their attachment to oligonucleotides (Haugland, 1996; U.S. Pat. Nos. 3,996,345 and 4,351,760 and the like). Preferred quenchers are described in co-owned U.S. Pat. No. 6,727,356, incorporated herein by reference. Other quenchers include bis azo quenchers (U.S. Pat. No. 6,790,945) and dyes from Biosearch Technologies. Inc. (provided as Black Hole™ Quenchers: BH-1. BH-2 and BH-3). Dabcyl, TAMRA and carboxy tetramethyl rhodamine.

Minor groove binder oligonucleotide conjugates (or "probes") have been described (see U.S. Pat. No. 5,801,155 and U.S. Pat. No. 6,312,894, both hereby incorporated by reference). These conjugates form hyper-stabilized duplexes with complementary DNA. In particular, sequence specificity of short minor groove binder probes is excellent for high temperature applications such as PCR. The probes/conjugates of the present disclosure can also have a covalently attached minor groove binder. A variety of suitable minor groove binders have been described in the literature. See, for example, Kutyavin, et al. U.S. Pat. No. 5,801,155; Wemmer, D. E., and Dervan P. B., *Current Opinion in Structural Biology*, 7:355-361 (1997); Walker, W. L., Kopka, J. L. and Goodsell, D. S., *Biopolymers*, 44:323-334 (1997): Zimmer, C & Wahnert, U. *Prog. Biophys. Molec. Bio.* 47:31-112 (1986) and Reddy, B. S. P., Dondhi, S. M., and Lown, J. W., *Pharmacol. Therap.*, 84:1-111 (1999).

Suitable methods for attaching minor groove binders (as well as reporter groups such as fluorophores and quenchers) through linkers to oligonucleotides are described in, for example. U.S. Pat. Nos. RE 38.416; 5,512,677; 5,419,966; 5,696,251; 5,585,481; 5,942,610 and 5,736,626.

A nucleotide mono-phosphate, nucleotide di-phosphate or a nucleotide triphosphate processing enzyme is an enzyme that utilizes a nucleotide mono-phosphate, nucleotide di-phosphate or a nucleotide triphosphate as one of its substrates. A nucleotide mono-phosphate, a nucleotide di-phosphate or a nucleotide triphosphate nucleic acid processing enzyme catalyzes modifications to nucleic acids or nucleic acid intermediates using either a nucleotide mono-phosphate, nucleotide di-phosphate or a nucleotide triphosphate as one of the substrates. Nucleotide mono-phosphate, nucleotide di-phosphate or nucleotide triphosphate enzymes include but are not limited to primer extension enzymes. DNA polymerases, RNA polymerases, restriction enzymes, nicking enzymes, repair enzymes or ligation enzymes.

The synthesis of pyrazolopyrimidine-monophosphate and pyrazolopyrimidine-triphosphate analogs has been disclosed in U.S. Pat. No. RE 38,416.

The practice of the present invention will employ, unless otherwise indicated, conventional techniques in organic chemistry, biochemistry, oligonucleotide synthesis and modification, bioconjugate chemistry, nucleic acid hybridization, molecular biology, microbiology, genetics, recombinant DNA, sequencing, next generation sequencing and related fields as are within the skill of the art. These techniques are fully explained in the literature. See, for example. Sambrook, Fritsch & Maniatis. Molecular Cloning: A Laboratory Manual. Second Edition, Cold Spring Harbor Laboratory Press (1989): Lee H et al., Methods Mol. Biol. 855: 155-74 (2012); Ausubel, et al., Current Protocols In Molecular Biology. John Wiley & Sons (1987, 1988, 1989, 1990, 1991, 1992, 1993, 1994, 1995, 1996); Gait (ed.), Oligonucleotide Synthesis: A Practical Approach, IRL Press (1984); Eckstein (ed.), Oligonucleotides and Analogues: A Practical Approach, IRL Press (1991).

Amplification procedures are those in which man) copies of a target nucleic acid sequence are generated, usually in an exponential fashion, by sequential polymerization and/or ligation reactions. In addition to the more traditional amplification reactions discussed below, the present invention is useful in amplifications involving three-way junctures (see, WO 99/37085), signal amplification (see Capaldi, et al., *Nuc. Acids Res.* 28:E21 (2000)), T7 polymerases, reverse transcriptase. RNase H, RT-PCR. Rolling Circles, cleavase and the like. Isothermal amplification methods have been reviewed (Niemz, A. et al Trends Biotechnol., 29: 240-50 (2011)). The "term oligonucleotide primers adjacent to a probe region" refers to when 0 or one or more base separate the primer and probe. The term "overlapping with said probe region" is defined as disclosed in U.S. Pat. No. 7,319,022. The term "Ct" refers to the fractional PCR cycle number at which the reporter fluorescence is greater than the threshold.

Many amplification reactions, such as PCR, utilize reiterative primer-dependent polymerization reactions. A primer is a nucleic acid that is capable of hybridizing to a second, template nucleic acid and that, once hybridized, is capable of being extended by a polymerizing enzyme (in the presence of nucleotide substrates), using the second nucleic acid as a template. Polymerizing enzymes include, but are not limited to, DNA and RNA polymerases and reverse transcriptases, etc. Conditions favorable for polymerization by different polymerizing enzymes are well-known to those of skill in the art. See, for example. Sambrook et al. supra; Ausubel, et al., supra; Innis et al., supra. Generally, in order to be extendible by a polymerizing enzyme, a primer must have an unblocked 3"-end, preferably a free 3' hydroxyl group. The product of an amplification reaction is an extended primer, wherein the primer has been extended by a polymerizing enzyme.

II. Description

The present inosine analogues include monomeric compounds of Formula I and

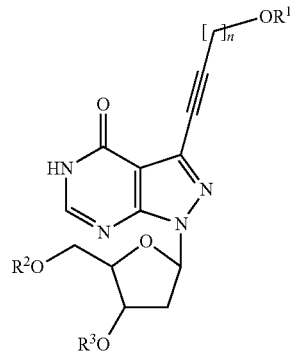

Formula I

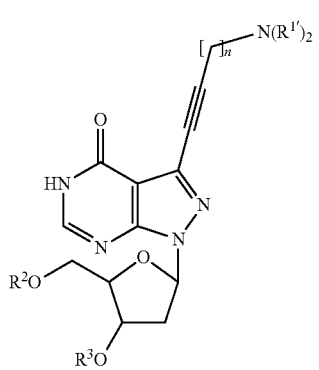

Formula II wherein:

R$^1$ is H or a protecting group;

R$^{1'}$ is H, alkyl, —(C=NR$^4$)N(R$^4$)$_2$, —(C=O)N(R$^4$)$_2$, or a protecting group;

R$^2$ is H, a phosphate group, a polyphosphate group, an activated phosphate group, a protecting group, phosphoramidite or a solid support;

R$^3$ is H, a protecting group, or a phosphoramidite;

R$^4$ is H or an alkyl; and n is 1 to 5.

In certain embodiments, such as when R$^2$ in the formulas above is a polyphosphate group, this resulting polyphosphate analog can be a diphosphate or triphosphate. These polyphosphate analogs can be used in enzyme catalyzed primer extension reactions.

In certain embodiments the present inosine analogues are also useful in oligomers and in intermediates for oligonucleotide synthesis. In particular, the inosine analogues can also include compounds of Formulas III and IV below:

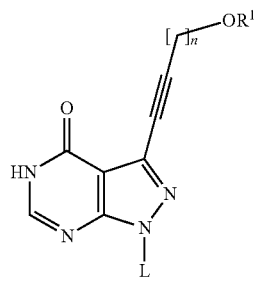

Formula III

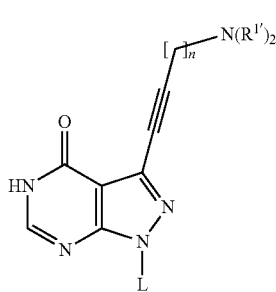

Formula IV wherein:

R$^1$ is H or a protecting group;

R$^{1'}$ is H, alkyl, —(C=NR$^4$)N(R$^4$)$_2$, —(C=O)N(R$^4$)$_2$, or a protecting group; and L is a sugar or sugar/phosphate backbone analogue, including but not limited to a backbone of DNA, RNA, PNA, locked nucleic acid, modified DNA, modified PNA, modified RNA, or any combination thereof.

In preferred embodiments, the modified oligonucleotides incorporating the present inosine analogues are comprised of glycosidic moieties, preferably 2-deoxyribofuranosides wherein all internucleoside linkages are the naturally occurring phosphodiester linkages. In alternative embodiments however, the 2-deoxy-β-D-ribofuranose groups are replaced with other sugars, for example, β-D-ribofuranose. In addition, β-D-ribofuranose may be present wherein the 2-OH of the ribose moiety is alkylated with a C$_{1-6}$ alkyl group (2-(O—C$_{1-6}$ alkyl)ribose) or with a C$_{2-6}$ alkenyl group (2-(O—C$_{1-6}$ alkenyl)ribose), or is replaced by a fluoro group (2-fluororibose). Related oligomer-forming sugars useful in the present invention are those that are "locked", i.e., contain a methylene bridge between C-4' and an oxygen atom at C-2'. Other sugar moieties compatible with hybridization of the oligonucleotide can also be used, and are known to those of skill in the art, including, but not limited to, α-D-arabinofuranosides, α-2'-deoxyribofuranosides or 2',3'-dideoxy-3'-aminoribofuranosides. Oligonucleotides containing α-D-arabinofuranosides can be prepared as described in U.S. Pat. No. 5,177,196. Oligonucleotides containing 2',3'-dideoxy-3'-aminoribofuranosides are described in Chen et al. 1995. Synthetic procedures for locked nucleic acids (Singh et al, 1998; Wengel J., 1998) and oligonucleotides containing 2'-halogen-2'-deoxyribofuranosides (Palissa et al. 1987) have been described. The phosphate backbone of the modified oligonucleotides described herein can also be modified so that the oligonucleotides contain phosphorothioate linkages and/or methylphosphonates and/or phosphoroamidates (Chen et al., 1995). Combinations of oligonucleotide linkages are also within the scope of the present invention. Still other backbone modifications are known to those of skill in the art.

In another group of embodiments, the inosine analogues described herein are incorporated into PNA and DNA/PNA chimeras to balance $T_m$s and provide modified oligonucleotides having improved hybridization properties. Various modified forms of DNA and DNA analogues have been used in attempts to overcome some of the disadvantages of the use of DNA molecules as probes and primers. Among these are peptide nucleic acids ("PNAs"), also known as polyamide nucleic acids (Nielsen et al. 1991). PNAs contain natural RNA and DNA heterocyclic base units that are linked by a polyamide backbone instead of the sugar-phosphate backbone characteristic of DNA and RNA. PNAs are capable of hybridization to complementary DNA and RNA target sequences and, in fact, hybridize more strongly than a corresponding nucleic acid probe. The synthesis of PNA oligomers and reactive monomers used in the synthesis of PNA oligomers have been described in U.S. Pat. Nos. 5,539,082; 5,714,331; 5,773,571; 5,736,336 and 5,766,855. Alternate approaches to PNA and DNA/PNA chimera synthesis and monomers for PNA synthesis have been summarized (Uhlmann et al. 1998). Accordingly, the use of any combination of normal bases, 3-alkynyl-1H-pyrazolo[3,4-d]pyrimidin-4(5H)-one analogue bases, universal bases and minor groove binders to balance the $T_m$ of a PNA or DNA/PNA chimera is in the scope of this invention. The synthetic methods necessary for the synthesis of modified base monomeric units required for PNA and PNA/DNA chimeras synthesis are available in this application and Uhlmann et al. 1998.

Figure 2:
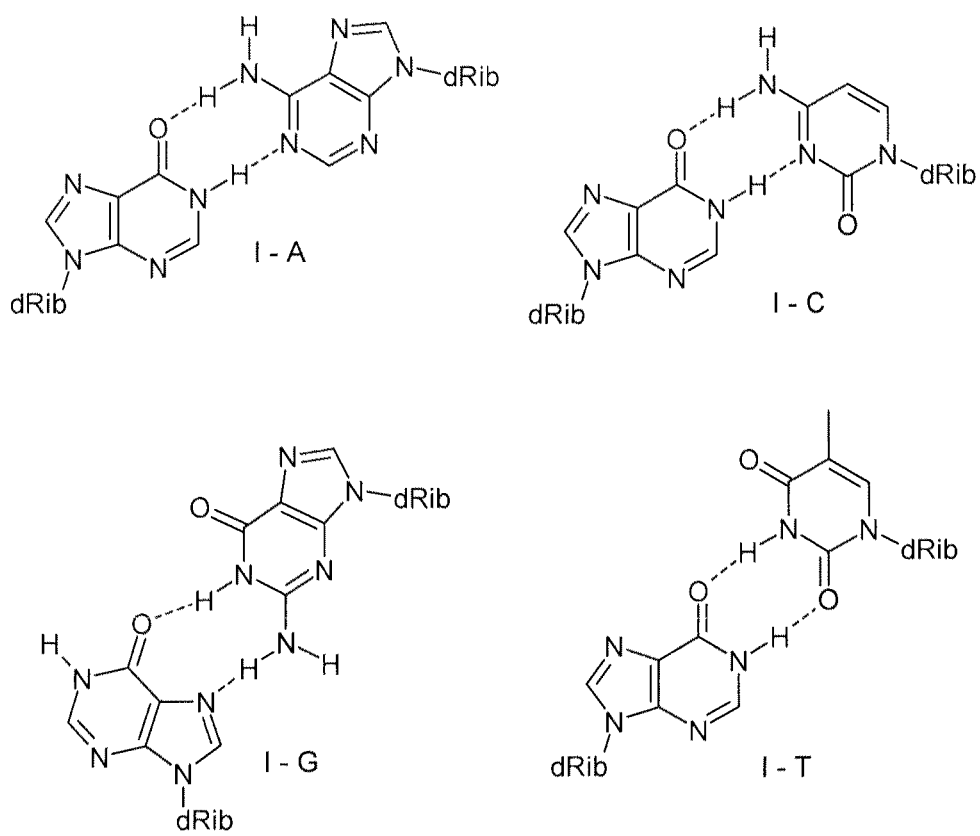
FIG. 2 shows the possible hydrogen bonds between hypoxanthine and the natural nucleic acid bases.
Figure 3:
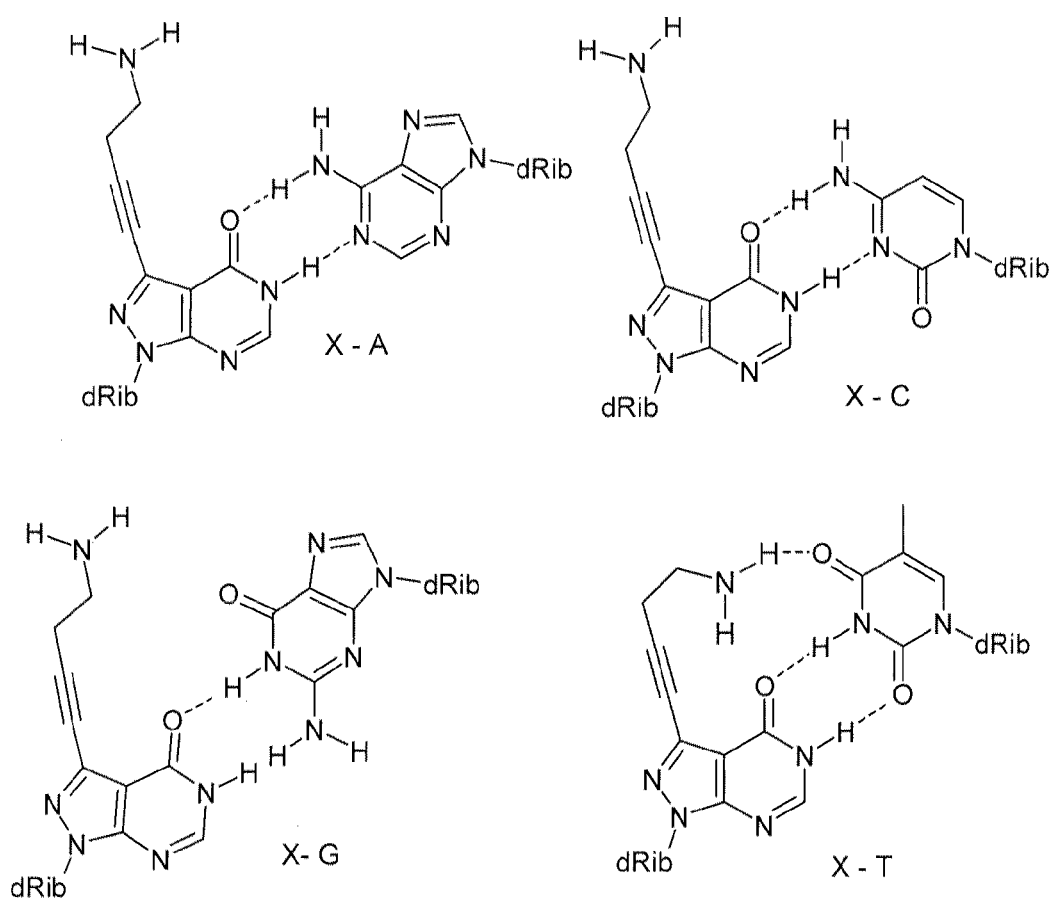
FIG. 3 shows, without being bound by theory, proposed hydrogen bonds between 3-(aminobutynyl)-1H-pyrazolo[3,4-d]pyrimidin-4(5H)-one and the normal nucleic bases.

Example compounds of the invention are shown in FIG. 1. FIG. 2 illustrates the hydrogen bonds that occur between hypoxathine and the natural nucleic acid basis. As indicated, and without being bound by theory, those skilled in the art view hypoxanthine as forming two hydrogen bonds with the normal nucleic acid bases in duplex formation. FIG. 3 illustrates, again without being bound by theory, proposed hydrogen bond formation with $NH_2Bu$-PPI with natural bases in a duplex.

The present 3-alkynyl-1H-pyrazolo[3,4-d]pyrimidin-4(5H)-one-based analogues function unexpectedly well as universal bases. Not only do they stabilize duplexes substantially more than hypoxanthine opposite A, C, and T but they are also recognized in primers by polymerases, allowing efficient amplification. In the case of G, binding is similar to that observed with inosine.

The unexpected properties of the 3-alkynyl-1H-pyrazolo[3,4-d]pyrimidin-4(5H)-one-based analogues of the present invention may be applied to essentially any methodologies that are based on nucleic acid hybridization and/or involve participation of nucleic acid processing enzymes. The term nucleic acid processing enzyme concerns any enzyme that is involved in a chemical transformation or physical manipulation of nucleic acids or their components. Accordingly, the 3-alkynyl-1H-pyrazolo[3,4-d]pyrimidin-4(5H)-one-based analogues are useful in all hybridization based techniques, including but not limited to detection of more than one target, amplification of more than one target, use of arrays, use of processing enzymes, conversion of intermediates, sequencing, and others.

The present disclosure pertains, in one aspect, to a method for continuous monitoring of polynucleotide amplification of a target nucleic acid sequence the method comprising:

(a) combining a sample containing said target nucleic acid with one or more oligonucleotide primers adjacent to or overlapping with said probe region of the target sequence, a polymerizing enzyme, nucleotide substrates, and a nucleic acid oligomer of between 5 and 100 bases long wherein said nucleic acid polymer has a backbone component selected from the group consisting of a sugar phosphate backbone, a modified sugar phosphate backbone, a locked nucleic acid backbone, a peptidic backbone or a variant thereof used in nucleic acid preparation; and at least one nucleic acid base is substituted with a 3-alkynyl-1H-pyrazolo[3,4-d]pyrimidin-4(5H)-one analogue and the oligonucleotide portion has a sequence complementary to a portion of the target sequence being amplified, to provide a mixture;

(b) incubating the mixture under conditions favorable for polymerization; and (c) continuously monitoring the amplification by monitoring the fluorescence produced upon conjugate hybridization to the amplified target.

In some embodiments at least one of said oligonucleotide primers has a sequence complementary to an adjacent portion of the probe region of the target nucleic acid sequence.

In some embodiments the method for continuous monitoring of polynucleotide amplification of a target nucleic acid sequence includes methods in which each base independently represents a nucleic acid base, at least one 3-alkynyl-1H-pyrazolo[3,4-d]pyrimidin-4(5H)-one analogue, and at least one modified base.

In other embodiments the nucleic acid oligomer is a conjugate comprising a minor groove binder ligand.

Another embodiment pertains to a method for continuous monitoring of polynucleotide amplification of a target nucleic acid sequence, the method comprising one or more oligonucleotide primers adjacent to or overlapping with said probe region of the target sequence, wherein said one or more oligonucleotide primers is an oligonucleotide is between 5 and 50 bases long wherein said nucleic acid polymer has a backbone component selected from the group consisting of a sugar phosphate backbone, a chimeric modified sugar phosphate backbone, chimeric locked nucleic acid backbone, a chimeric peptidic backbone or a variant thereof used in nucleic acid amplification; and at least one nucleic acid base is substituted with a 3-alkynyl-1H-pyrazolo[3,4-d]pyrimidin-4(5H)-one analogue and the oligonucleotide portion has a sequence complementary to a portion of the target sequence being amplified.

Another method for primer extension of nucleic acids targets comprises one or more primers complementary to the target sequence, wherein each nucleic acid base independently represents a nucleic acid base, at least one 3-alkynyl-1H-pyrazolo[3,4-d]pyrimidin-4(5H)-one analogue and at least one modified base In additional embodiments the primer also contains a minor groove binder ligand and a label.

An alternative method for continuous monitoring of polynucleotide amplification of a target nucleic acid sequence comprises one or more oligonucleotide primers adjacent to or overlapping with said probe region of the target sequence, wherein each nucleic acid base independently represents a nucleic acid base, at least one 3-alkynyl-1H-pyrazolo[3,4-d]pyrimidin-4(5H)-one analogue and at least one modified base.

In another embodiment multiple nucleic acid targets are detected in a polymerase amplification reaction with one or more primers and more than one probe where each such probe is uniquely labeled and wherein at least one of said primers or probe contains at least one normal base substituted with a 3-alkynyl-1H-pyrazolo[3,4-d]pyrimidin-4(5H)-one analogue.

In another aspect, the present disclosure pertains to a method for distinguishing between wild-type, mutant and heterozygous target polynucleotides, the method comprising:

a) measuring the fluorescence emission as a function of temperature to determine a first melting profile of a first probe melting from a first amplified polynucleotide and a second melting profile of a second probe melting from a second amplified polynucleotide wherein each probe independently contains zero or one or more 3-alkynyl-1H-pyrazolo[3,4-d]pyrimidin-4(5H)-one analogues; and (b) comparing the first melting curve to the second melting curve.

In other embodiments, the sample is further contacted with a set of primers under amplification conditions and where at least one of the primers contains at least one 3-alkynyl-1H-pyrazolo[3,4-d]pyrimidin-4(5H)-one analogues. In other embodiments at least one of the primers may also contain one modified base selected from the group disclosed above.

In other embodiments, a method is provided for continuous monitoring of poly nucleotide amplification of a target nucleic acid sequence having at least two single nucleotide polymorphisms wherein a first single nucleotide polymorphism is to be distinguished and a second single nucleotide polymorphism is not distinguished, each of said polymorphisms being in a probe region of said target nucleic acid, comprising:

(a) combining a sample containing said target nucleic acid with one or more oligonucleotide primers adjacent to or overlapping with said probe region of the target sequence, a polymerizing enzyme, nucleotide substrates, and an oligonucleotide conjugate comprising a fluorophore, wherein the oligonucleotide conjugate has a nucleic acid backbone component selected from the group consisting of a sugar phosphate backbone, a modified sugar phosphate backbone, a locked nucleic acid backbone, and a peptidic backbone, wherein the oligonucleotide conjugate contains a nucleic acid base substituted with a 3-alkynyl-1H-pyrazolo[3,4-d]pyrimidin-4(5H)-one analogue at the site complementary to said second single nucleotide polymorphism, and wherein the oligonucleotide conjugate has a sequence complementary to a portion of the target sequence being amplified, to provide a mixture;

(b) incubating the mixture under conditions favorable for polymerization; and (c) continuously monitoring the amplification by monitoring the fluorescence produced upon conjugate hybridization to the amplified target.

In other embodiments the polymerization is catalyzed by a polymerizing enzyme under isothermal conditions.

In certain embodiments a nucleotide comprising a 3-alkynyl-1H-pyrazolo[3,4-d]pyrimidin-4(5H)-one analogue as disclosed herein is incorporated by a nucleotide processing enzyme into a nucleic acid, where said nucleic acid as a result has improved hybridization properties when hybridized to a second nucleic acid. Incorporated 3-alkynyl-1H-pyrazolo[3,4-d]pyrimidin-4(5H)-one analogues of the invention have universal properties including improved hybridization ($T_m$s) particularly with A, C and T. While the present analogues will hybridize to G, they typically show no improvement in hybridization compared to inosine.

Also provided are oligomer microarrays wherein at least one of the oligomers described herein is present on the array. Thus, modified oligomers comprising 3-alkynyl-1H-pyrazolo[3,4-d]pyrimidin-4(5H)-one analogues as disclosed herein, are useful in techniques including, but not limited to, hybridization, primer extension, hydrolyzable probe assays, amplification methods (e.g. PCR, SSSR, NASBA, SDA, LAMP), single nucleotide mismatch discrimination, allele-specific oligonucleotide hybridization, nucleotide sequence analysis, hybridization to oligonucleotide arrays, in situ hybridization and related techniques. Oligomers disclosed herein can be used as immobilized oligomers in oligomer arrays such as those described in, for example, U.S. Pat. Nos. 5,492,806; 5,525.464; 5,556.752 and PCT publications WO 92/10588 and WO 96/17957.

In other embodiments sequencing primers contain one or more 3-alkynyl-1H-pyrazolo[3,4-d]pyrimidin-4(5H)-one analogue bases.

Accordingly, in another aspect of the invention, kits are provided that contain probes and/or conjugates as described above, along with primers for amplification reactions, wherein the primers contain one or more 3-alkynyl-1H-pyrazolo[3,4-d]pyrimidin-4(5H)-one analogue bases, more preferably, from one to ten 3-alkynyl-1H-pyrazolo[3,4-d]pyrimidin-4(5H)-one bases per primer.

III. Synthesis

Figure 4:
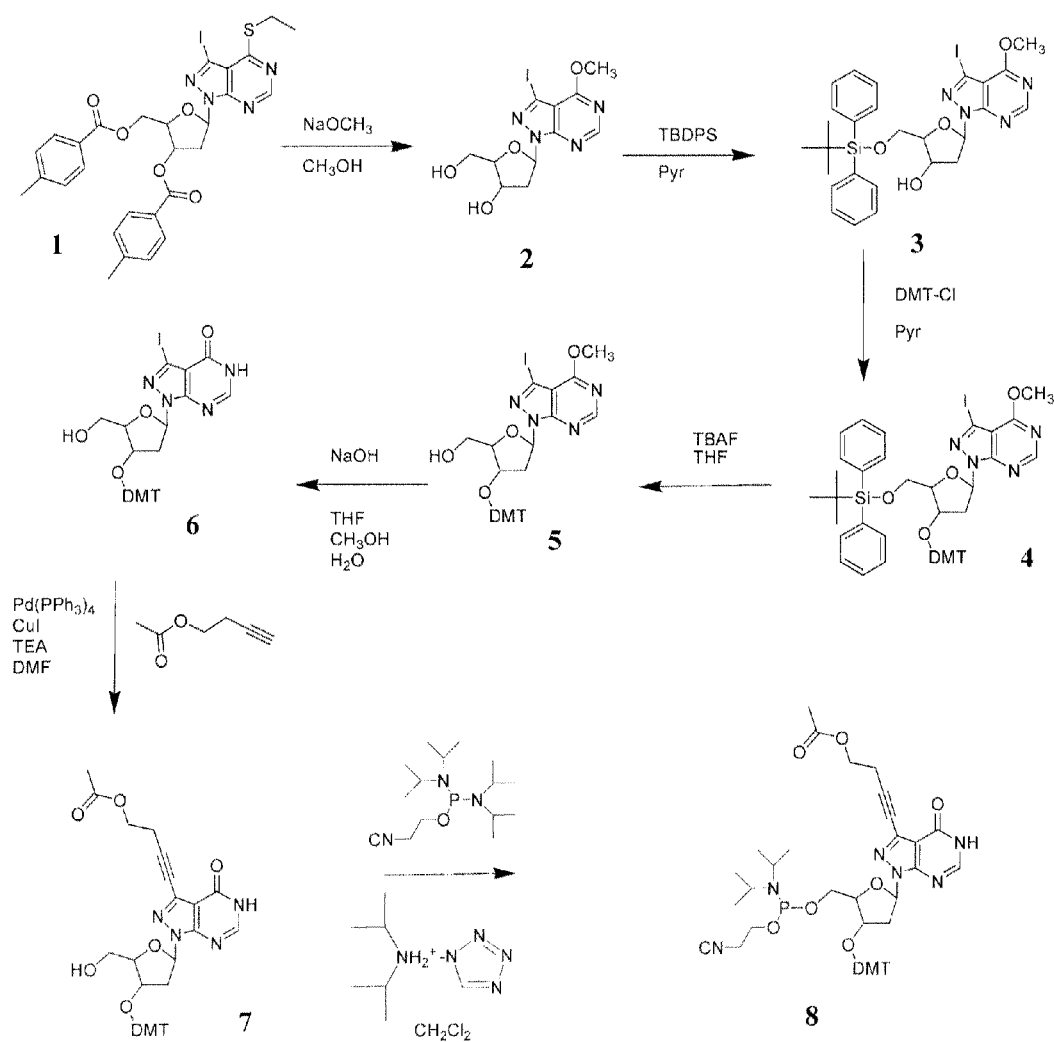
FIG. 4 shows a reaction scheme for synthesis of a protected (2-deoxy-β-D-ribofuranosyl)-3-hydroxybuynyl-1H-pyrazolo[3,4-d]pyrimidin-4(5H)-one 5'-phosphoramidite.

Synthesis of (2-deoxy-β-D-ribofuranosyl)-3-alkynyl-1H-pyrazolo[3,4-d]pyrimidin-4(5H)-ones The synthesis of the protected (2-deoxy-β-D-ribofuranosyl)-3-hydroxybuynyl-1H-pyrazolo[3,4-d]pyrimidin-4(5H)-on 5'-phosphoramidite 8 is shown in Reaction Scheme 1, in FIG. 4. Briefly compound 1 (U.S. Pat. No. 6,949,367) was converted to 3-iodo-4-methoxy-1H-pyrazolo[3,4-d]pyrimidine 2 by reaction with sodium methoxide in methanol. Then the 5'-hydroxyl group was protected with a tert-butyldiphenylsilyl group by the reaction with TBDPS in pyridine to yield 3. The 3'-hydroxyl was then protected with a dimethoxytrityl group by reaction of dimethoxytrityl chloride in anhydrous pyridine to produce 4. Treatment of 4 with tetrabutylammonium fluoride in THF removed the tert-butyldiphenylsilyl group to yield 5, which was converted to the pyrazolopyrimidine-inosine analogue 6 by treatment with an aqueous sodium hydroxide-THF/methanol solution. Compound 6 was converted to 3-(4-acetoxybutynyl)-analogue 7 by reaction with but-3-ynyl acetate in the presence of CuI and Pd(PPh$_3$)$_4$ in anhydrous DMF. The protected phosphoramidite 8 was synthesized by reaction of 7 with 2-cyano-N,N,N',N'-tetraisopropylphordiamidite and diisopropylammonium tetrazolide in CH$_2$Cl$_2$.

Figure 5:
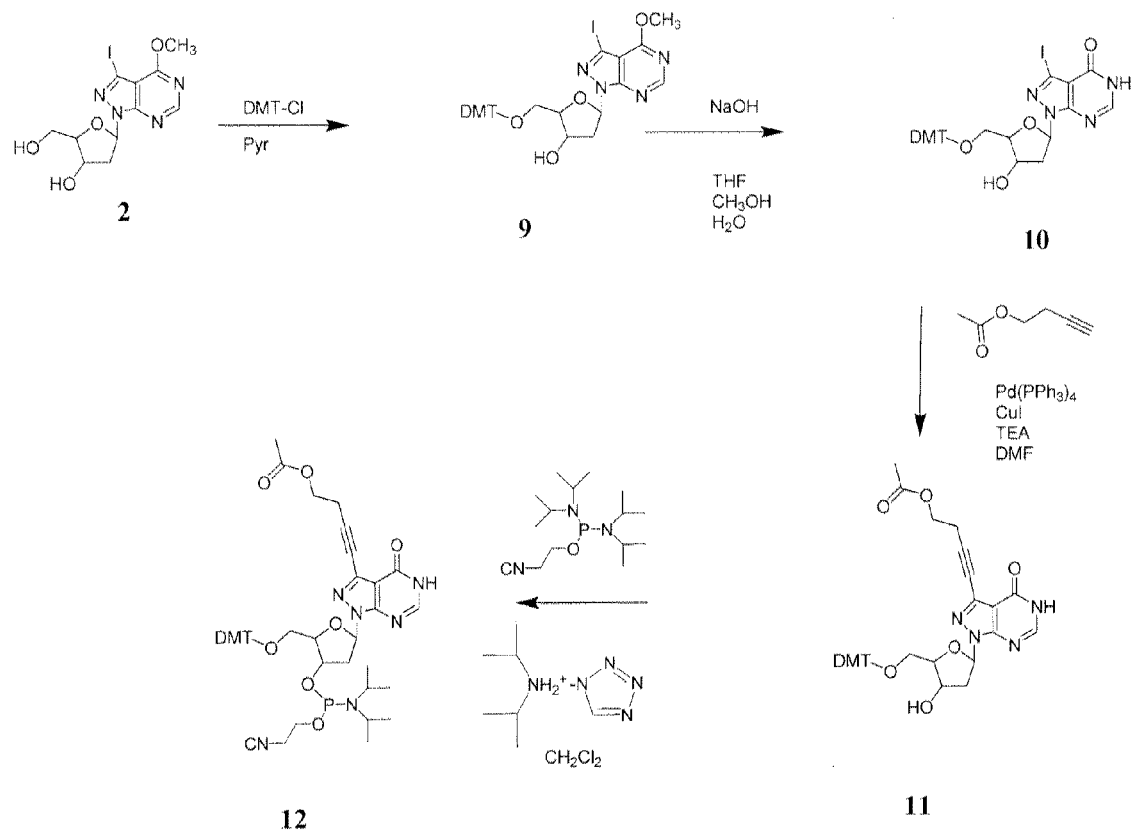
FIG. 5 shows a reaction scheme for synthesis of a protected (2-deoxy-8-D-ribofuranosyl)-3-hydroxybuynyl-1H-pyrazolo[3,4-d]pyrimidin-4(5H)-one 3'-phosphoramidite.

The synthesis of the protected (2-deoxy-β-D-ribofuranosyl)-3' hydroxybuynyl-1H-pyrazolo[3,4-d]pyrimidin-4(5H)-on 3'-phosphoramidite 12 is shown in Reaction Scheme 2, in FIG. 5.

The 3'-hydroxy of 3-Iodo-4-methoxy-1H-pyrazolo[3,4-d]pyrimidine 2 was protected with a dimethoxytrityl group by reaction of dimethoxytrityl chloride in anhydrous pyridine to produce 9. Compound 9 was converted to the pyrazolopyrimidine-inosine analogue 10 by treatment with an aqueous sodium hydroxide-THF/methanol solution which was then converted to 3-(4-acetoxybutynyl)-analogue 11 by reaction with but-3-ynyl acetate in the presence of CuI and Pd(PPh$_3$)$_4$ in anhydrous DMF. The protected phosphoramidite 12 was synthesized by reaction of 11 with 2-cyano-N,N,N',N'-tetraisopropylphordiamidite and diisopropylammonium tetrazolide in CH$_2$Cl$_2$.

Figure 6:
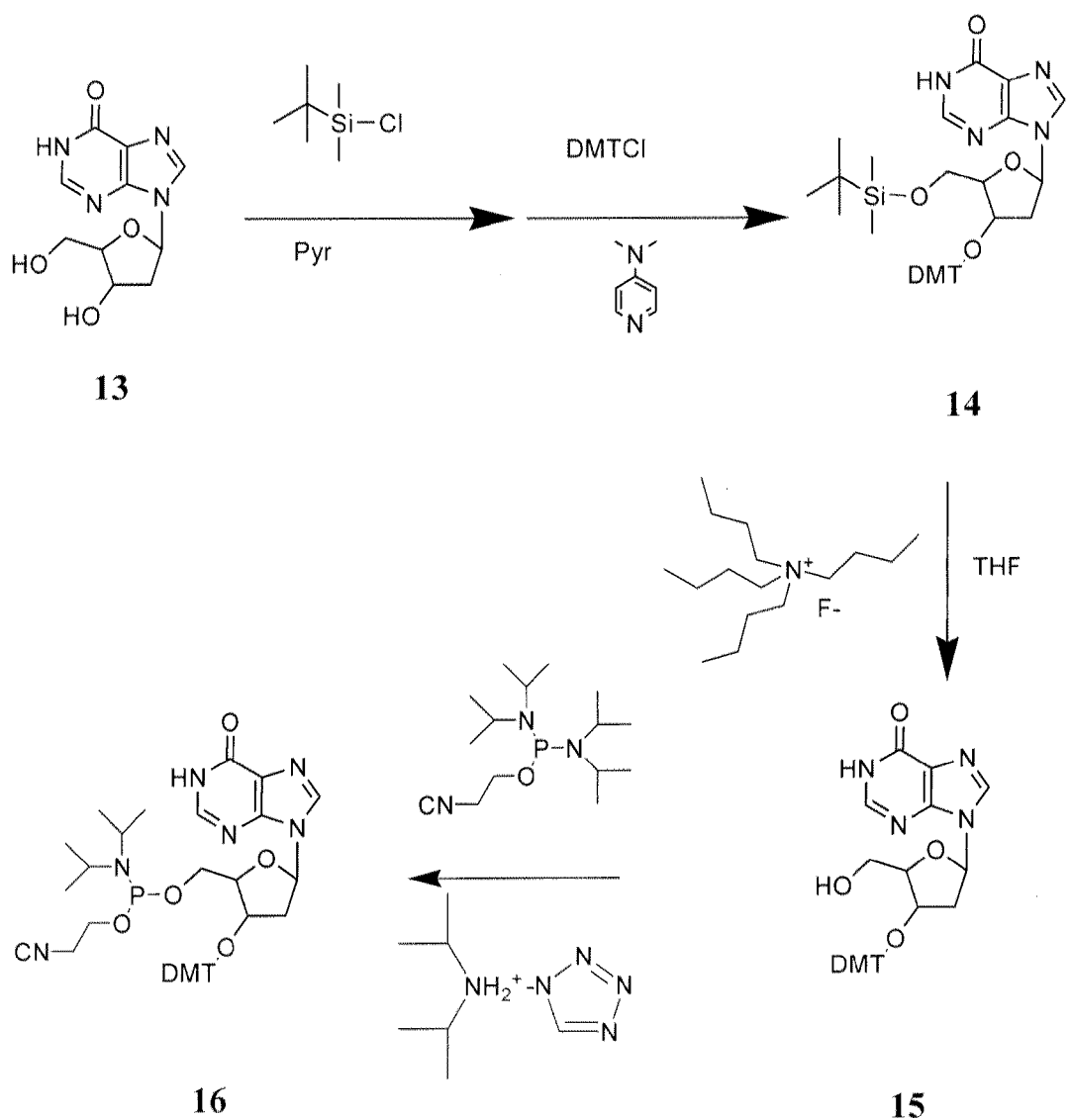
FIG. 6 shows a reaction scheme for synthesis of a protected inosine 5'-phosphoramidite.

The synthesis of the protected inosine 5'-phosphoramidite 16 is shown in Reaction Scheme 3, in FIG. 6.

The 5'-hydroxy of 2'-deoxyinosine (13) was first blocked with tert-butyldiphenylsilyl group and the 3'-hydroxyl was blocked with a DMT group as described above to yield 14. The silyl group of 14 was then removed by reaction with tetrabutylammonium fluoride in THF to give the DMT analogue 15 which was then converted to the phosphoramidite 16 as described above.

Figure 7:
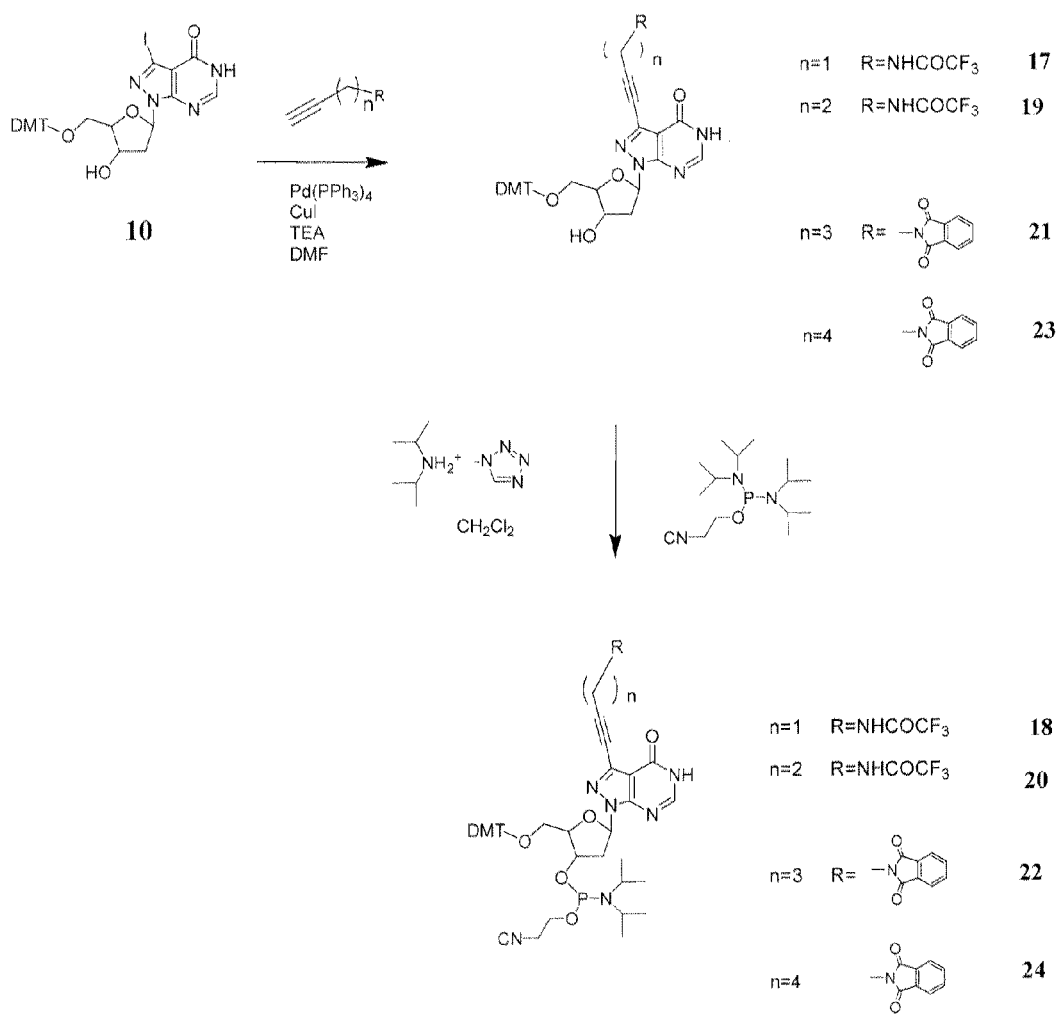
FIG. 7 shows a reaction scheme for synthesis of protected (2-deoxy-β-D-ribofuranosyl)-3-(aminoalkynyl)-1H-pyrazolo[3,4-d]pyrimidin-4(5H)-one analogues.

The synthesis of the protected (2-deoxy-β-D-ribofuranosyl)-3-(aminoalkynyl)-1H-pyrazolo[3,4-d]pyrimidin-4(5H)-one analogues is shown in Reaction Scheme 4, in FIG. 7.

Compounds 17, 19, 21 and 23 were prepared by Sonogashira coupling of compound 10 with trifluoroacetamido (n=1 and 2) or phthalimidoalkynyls (n=3 and 4). The following reaction with 2-cyanoethyl tetraisopropyl phosphordiamidite afforded final phosphoramidites 18, 20, 22 and 24.

Figure 8:
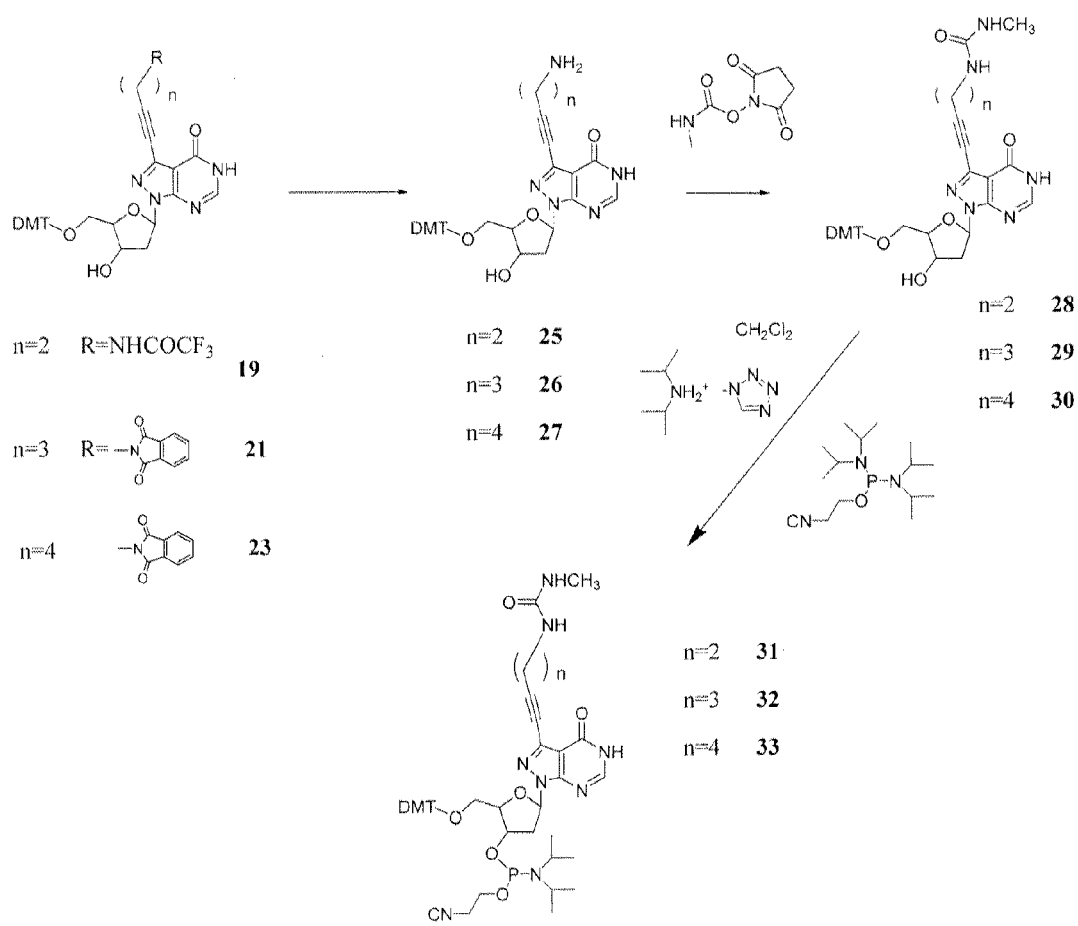
FIG. 8 shows a reaction scheme for synthesis of (2-deoxy-β-D-ribofuranosyl)-3-(methylcarbamoyloalkynyl)-1H-pyrazolo[3,4-d]pyrimidin-4(5H)-one analogues.

The synthesis of the (2-deoxy-β-D-ribofuranosyl)-3-(methylcarbamoyloalkynyl)-1H-pyrazolo[3,4-d]pyrimidin-4(5H)-one analogues is shown in Reaction Scheme 5, in FIG. 8.

Amines 25, 26 and 27 were prepared from the protected amine intermediates 19, 21 and 23 by a treatment with a mixture of aqueous methylamine and concentrated ammonium hydroxide at 55° C. under pressure. The free amines were converted into methylcarbomoyl derivatives 28, 29 and 30 by a reaction with N-succinimidyl N-methylcarbomate. The resulting 3'-hydroxy intermediates were reaction with 2-cyanoethyl tetraisopropylphosphordiamidite to afford final phosphoramidites 31, 32 and 23.

Figure 9:
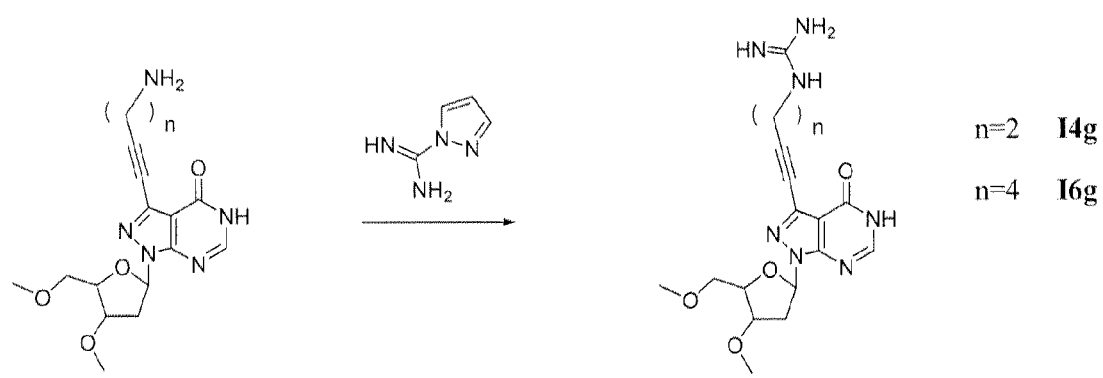
FIG. 9 shows a reaction scheme for synthesis of (2-deoxy-β-D-ribofuranosyl)-1H-pyrazolo[3,4-d]pyrimidin-4(5H)-one analogues bearing guanidinoalkynyl substituates at the 3-position of the nucleobase.
Figure 11:
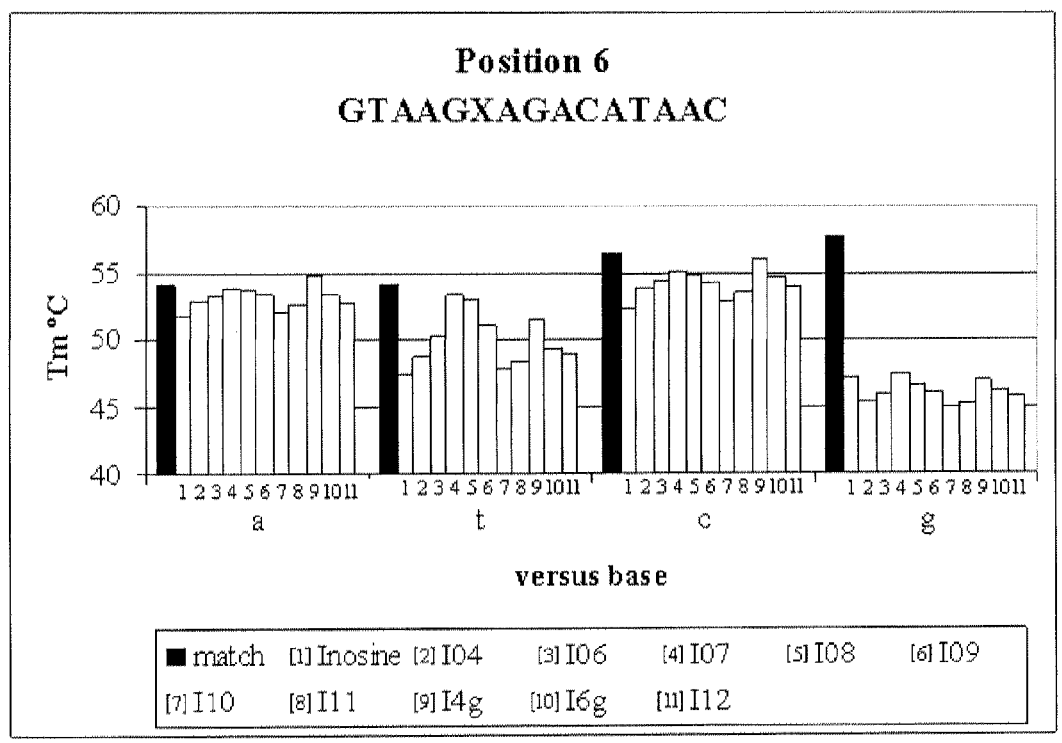
FIG. 11 shows a comparison of $T_m$s of duplexes between the 15-mer GTAAGXAGACATAAC (SEQ ID NO:2), where X is independently 2"-deoxinosine or a 2-deoxy-β-D-ribofuranosyl-3-alkynyl-1H-pyrazolo[3,4-d]pyrimidin-4(5H)-one of the present disclosure, and the complement which contains either A, T, C or G opposite to X.
Figure 12:
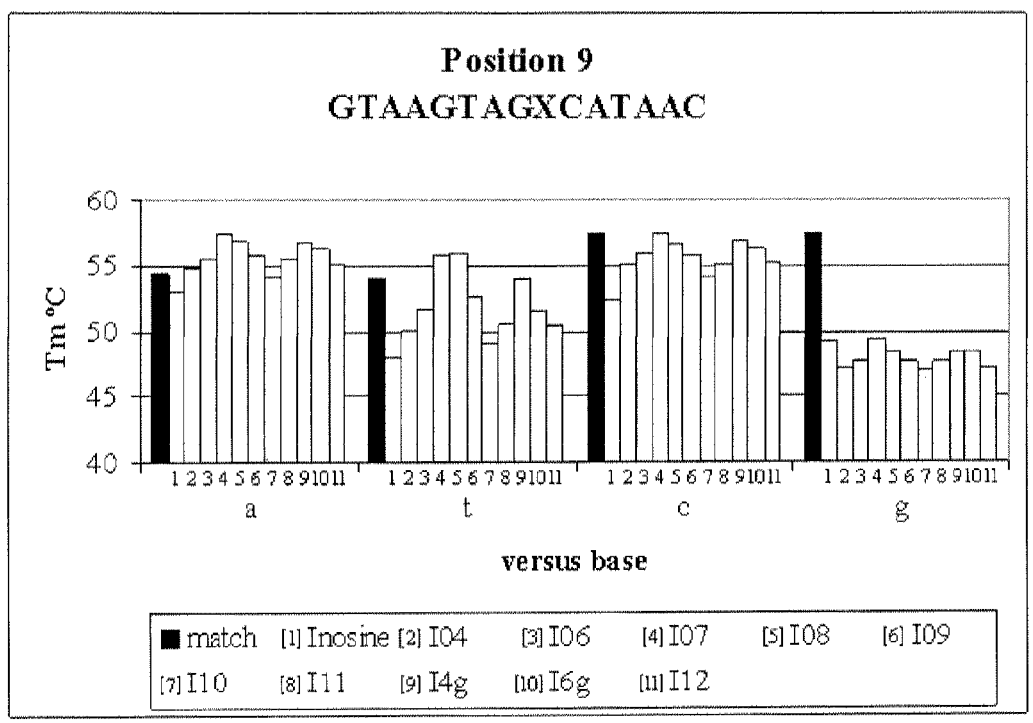
FIG. 12 shows a comparison of $T_m$s of duplexes between the 15-mer GTAAGTAGXCATAAC (SEQ ID NO:3), where X is independently 2'-deoxinosine or a 2-deoxy-β-D-ribofuranosyl-3-alkynyl-1H-pyrazolo[3,4-d]pyrimidin-4(5H)-one of the present disclosure, and the complement which contains either A, T, C or G opposite to X.
Figure 13:
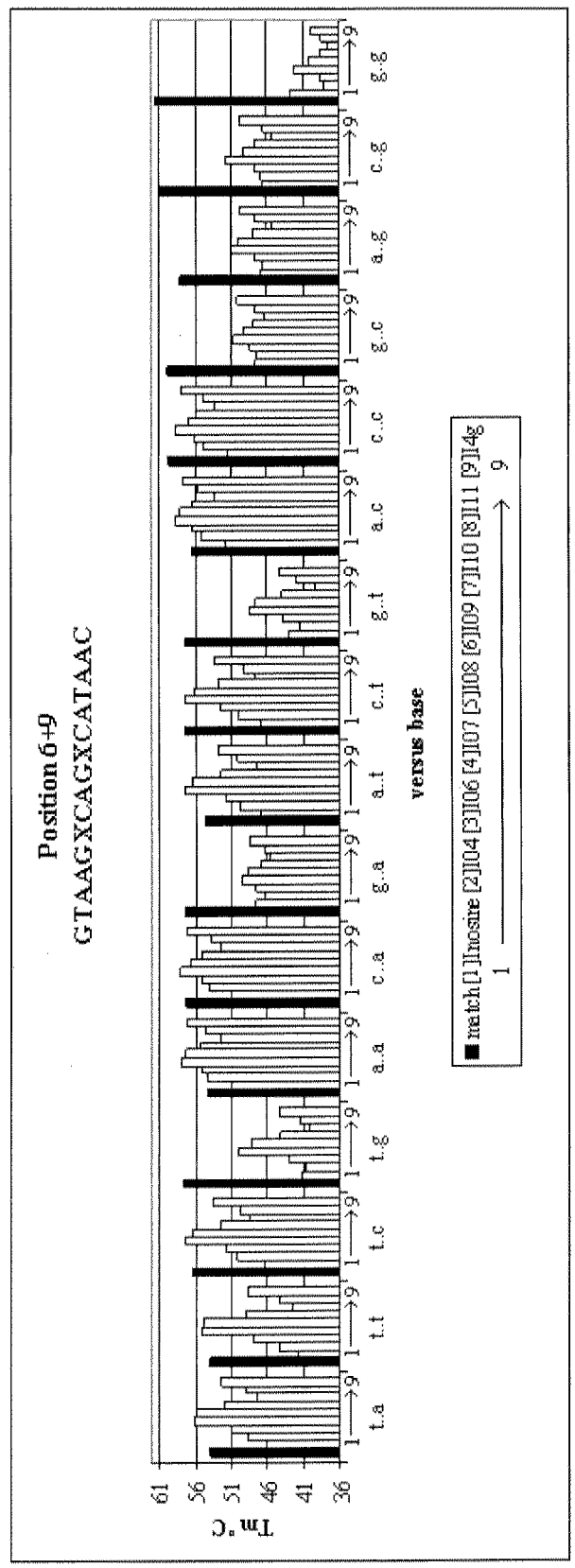
FIG. 13 shows a comparison of $T_m$s of duplexes between the 15-mer GTAAGXAGXCATAAC (SEQ ID NO:1), where X is independently 2'-deoxinosine, or a 2-deoxy-β-D-ribofuranosyl-3-alkynyl-1H-pyrazolo[3,4-d]pyrimidin-4(5H)-one of the present disclosure, and the complement which contains either A, T, C or G opposite to X.

Reaction Scheme 6, in FIG. 9, shows the preparation of (2-deoxy-β-D-ribofuranosyl)-1H-pyrazolo[3,4-d]pyrimidin-4(5H)-one analogues bearing guanidinoalkynyl substituates at the 3-position of the nucleobase.

EXAMPLES

The following examples are provided to illustrate, but not to limit, the presently claimed invention.

Example 1

Synthesis

This example illustrates the synthesis of the protected (2-deoxy-β-D-ribofuranosyl)-3-hydroxybuynyl-1H-pyrazolo[3,4-d]pyrimidin-4(5H)-one 5'-phosphoramidite 8.

1-(2-Deoxy-β-D-ribofuranosyl)-3-iodo-4-methoxy-1H-pyrazolo[3,4-d]pyrimidine (2)

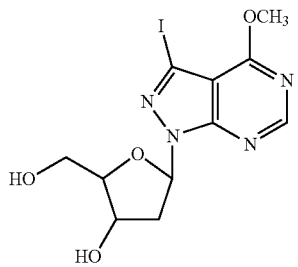 [SMILES: COc1ncnc2c1c(I)nn2C1CC(O)C(CO)O1]

In a 500 mL flask were combined 1 (U.S. Pat. No. 6,949,367) (5.6 g, 8.5 mmol) and sodium methoxide solution in methanol (56 mL, 25% NaOCH$_3$) and the suspension was sonicated for 25 minutes to obtain a hazy suspension. HPLC analysis showed the complete conversion of 1 to 2 and the flask was cooled, then glacial acetic acid (15.5 mL) was added and the mixture was concentrated on a rotary evaporator equipped with a bleach trap. The resulting solid was dissolved in 300 mL ethyl acetate and extracted with 150 mL water until solids dissolved. The organic layer was washed with brine (3×50 mL) and the pooled aqueous extracts were backwashed with ethyl acetate. The combined organic layers were dried over MgSO$_4$ and concentrated and suspended in hexanes for 14 h, filtered and washed with hexanes to obtain 2 as an off-white amorphous solid (3.16 g, 95% yield).

1-(5-(tert-Butyldiphenylsilyl)-2-deoxy-β-D-ribofuranosyl)-3-iodo-4-methoxy-1H-pyrazolo[3,4-d]pyrimidine (3)

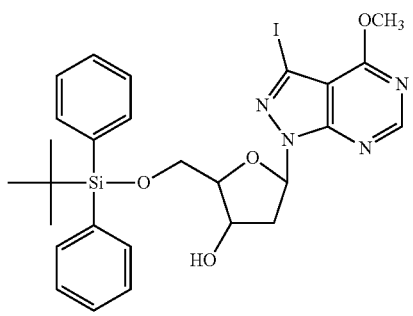 [SMILES: COc1ncnc2c1c(I)nn2C1CC(O)C(CO[Si](c2ccccc2)(c2ccccc2)C(C)(C)C)O1]

In a 500 mL flask was suspended 2 (3.6 g, 9.2 mmol) in anhydrous pyridine (60 mL), then tert-butyldiphenylchlorosilane (2.78 g, 10 mmol) was added and the mixture stirred for 72 hours. The suspension was concentrated and partitioned between ethyl acetate and water. The organic layer was washed with 10% citric acid, brine, dried over MgSO$_4$, and concentrated to a white foam. The crude product was purified by flash chromatography with 25-33% ethyl acetate in hexanes to obtain 3 as a white foam (5.2 g, 90% yield).

1-(5-(tert-Butyldiphenylsilyl)-3-dimethoxytrityl-2-deoxy-β-D-ribofuranosyl)-3-iodo-4-methoxy-1H-pyrazolo[3,4-d]pyrimidine (4)

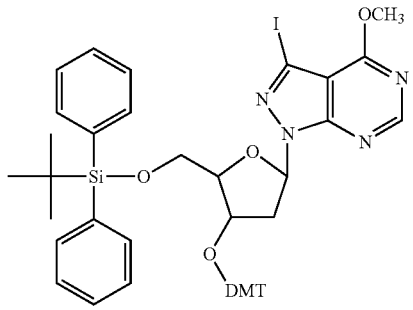

In a 500 mL flask was suspended 3 (5.15 g, 8.16 mmol) in anhydrous pyridine (60 mL), then 4,4'-dimethoxytrityl chloride (3.6 g, 10.6 mmol) was added and the mixture stirred for 14 hours. The reaction was titrated with additional 4,4'-dimethoxytrityl chloride until complete, then the mixture was concentrated and partitioned between ethyl acetate and water. The organic layer was washed with 10% citric acid, brine, dried over MgSO$_4$, and concentrated to obtain a bright yellow foam. The crude product was purified by flash chromatography with 10-25% ethyl acetate in hexanes to obtain 4 as a white foam (8.6 g, 113% yield).

1-(3-Dimethoxytrityl-2-deoxy-β-D-ribofuranosyl)-3-iodo-4-methoxy-1H-pyrazolo[3,4-d]pyrimidine (5)

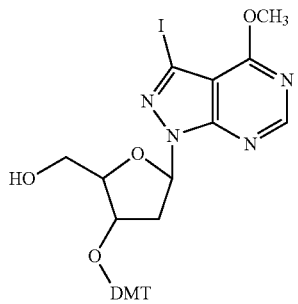

In a 500 mL flask was dissolved 4 (7.5 g, 8.0 mmol) in tetrabutylammonium fluoride in THF (16 mL, 1 M) and diluted with 20 mL THF. The reaction was stirred for 1 h and concentrated to a solid. The crude product was purified by flash chromatography using 10-60% ethyl acetate in hexanes to obtain 5 as a white foam (5.59 g, 100% yield).

1-(3-Dimethoxytrityl-2-deoxy-β-D-ribofuranosyl)-3-iodo-1H-pyrazolo[3,4-d]pyrimidin-4(5H)-one (6)

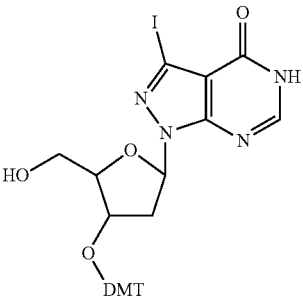

In a 500 mL flask was dissolved 5 (7.5 g, 8.0 mmol) in THF (27 mL), then added methanol (30 mL) and 50% NaOH$_{(aq)}$ (6 mL). The solution was heated at 40-45° C. for 6 hours, concentrated to a solid, and partitioned between ethyl acetate and 10% citric acid. The organic layer was washed with saturated NaHCO$_{3(aq)}$, brine, dried over MgSO$_4$ and concentrated to a pink-tinted foam. The crude product was purified by flash chromatography using 20-100% ethyl acetate in hexanes to obtain 6 as a white foam (5.15 g, 94% yield).

1-(3-Dimethoxytrityl-2-deoxy-β-D-ribofuranosyl)-3-(4-acetoxybut-1-yn-1-yl)-1H-pyrazolo[3,4-d]pyrimidin-4(5H)-one (7)

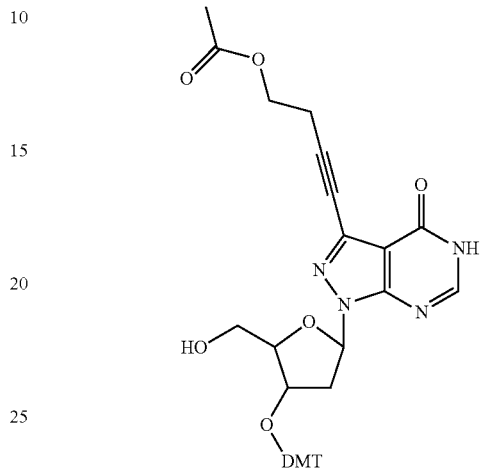

In a 500 mL flask was dissolved 6 (5.04 g, 7.4 mmol) in anhydrous DMF (40 mL), then added triethylamine (3 g, 30 mmol), but-3-ynyl acetate (1.0 g, 8.9 mmol), and the solution was degassed with argon. The flask was then charged with CuI (282 mg, 1.48 mmol) and Pd(PPh$_3$)$_4$ (855 mg, 740 μmol) and the reaction stirred for 14 h under argon. The orange solution was concentrated to a brown oil and purified by flash chromatography using 75-100% ethyl acetate in hexanes to obtain 7 as a pale yellow foam (3.7 g, 75% yield).

1-(5-(2-Cyanoethyl-N,N-diisopropyl)phosphoramidito-3-dimethoxytrityl-2-deoxy-β-D-ribofuranosyl)-3-(4-acetoxybut-1-yn-1-yl)-1H-pyrazolo[3,4-d]pyrimidin-4(5H)-one (8)

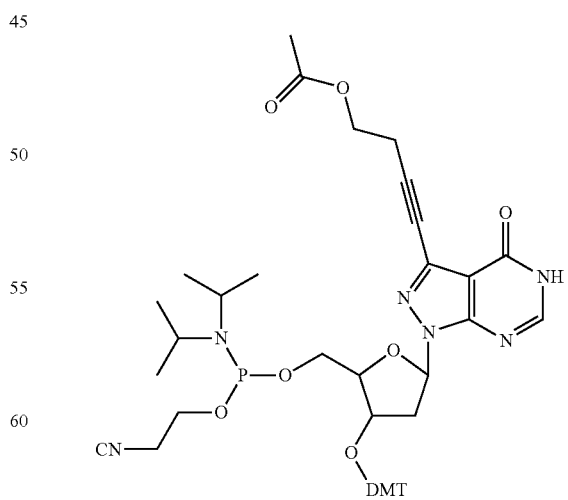

In a 500 mL flask was dissolved 7 (3.6 g, 5.4 mmol) in anhydrous CH$_2$Cl$_2$ (75 mL), then added diisopropylammonium tetrazolide (1.0 g, 5.9 mmol) and 2-cyanoethyl N,N,N', N'-tetraisopropylphosphordiamidite (2.55 mL, 8.1 mmol) and the reaction titrated with additional phosphoramidite reagent to completion. The suspension was concentrated and dissolved in ethyl acetate, washed with 5% NaHCO$_{3(aq)}$, brine, dried over Na$_2$SO$_4$, and concentrated to an oil. The crude product was dissolved in anhydrous ethyl acetate and precipitated with anhydrous pentane; the precipitation was repeated and the resulting gum was dried to obtain 8 as an amorphous solid (4.25 g, 91% yield).

Example 2

This example illustrates the synthesis of the protected (2-deoxy-β-D-ribofuranosyl)-3-hydroxybuynyl-1H-pyrazolo[3,4-d]pyrimidin-4(5H)-one 3*-phosphoramidite 12.

1-(5-Dimethoxytrityl-2-deoxy-β-D-ribofuranosyl)-3-iodo-4-methoxy-1H-pyrazolo[3,4-d]pyrimidine (9)

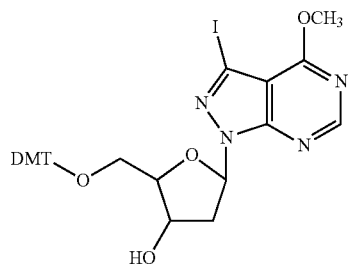

In a 500 mL flask was suspended 2 (3.16 g, 8.06 mmol) in anhydrous pyridine (60 mL), then 4,4'-dimethoxytrityl chloride (3.55 g, 10.5 mmol) was added and the reaction was stirred for 2 h. The solution was concentrated to a yellow oil, partitioned between ethyl acetate and 10% citric acid, and the organic layer was washed with saturated NaHCO$_{3(aq)}$, brine, MgSO$_4$, and concentrated to a yellow foam. The crude product was purified by flash chromatography using 25-75% ethyl acetate in hexanes to obtain 9 as a white foam (4.95 g, 88% yield).

1-(5-Dimethoxytrityl-2-deoxy-β-D-ribofuranosyl)-3-iodo-1H-pyrazolo[3,4-d]pyrimidin-4(5H)-one (10)

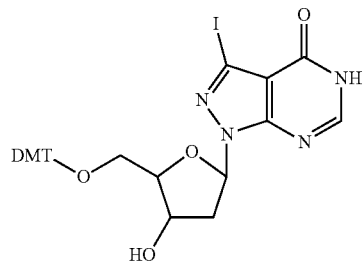

In a 500 mL flask was dissolved 9 (4.95 g, 7.1 mmol) in THF (25 mL), then added 50% NaOH$_{(aq)}$ (5.5 mL) and methanol (20 mL). Heat at 40-55° C. for 3 hours and concentrate the reaction mixture to a solid which was partitioned between ethyl acetate and 10% citric acid. The organic layer was washed with saturated NaHCO$_{3(aq)}$ and brine. The aqueous layers were backwashed with ethyl acetate, the combined organic layers dried over MgSO$_4$ and concentrated to a pale yellow foam. The crude product was purified by flash chromatography using 50-100% ethyl acetate in hexanes to obtain 10 as an off-white foam (4.8 g, 100% yield).

1-(5-Dimethoxy trityl-2-deoxy-β-D-ribofuranosyl)-3-(4-acetoxybut-1-yn-1-yl)-1H-pyrazolo[3,4-d]pyrimidin-4(5H)-one (11)

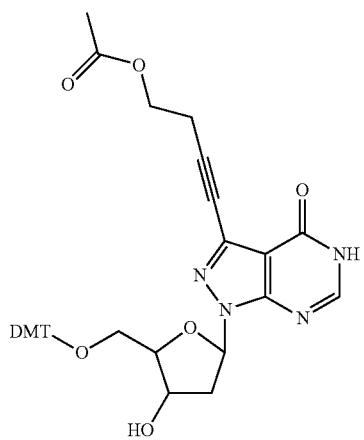

In a 500 mL flask was dissolved 10 (4.8 g, 7.1 mmol) in anhydrous DMF (40 mL), then added triethylamine (2.87 g, 28.4 mmol) and but-3-ynyl acetate (1.2 mL, 10.7 mmol). The solution was degassed under argon, then added CuI (324 mg, 1.7 mmol) and Pd(PPh$_3$)$_4$ (984 mg, 0.85 mmol) and the reaction stirred under argon for 72 hours then concentrated to a brown oil. The crude product was purified by flash chromatography using 50-100% ethyl acetate in hexanes. The impure product was chromatographed again using 3-15% methanol in dichloromethane then co-stripped with anhydrous CH$_3$CN to obtain 11 as an off-white solid (2.8 g, 59% yield).

1-(3-(2-Cyanoethyl-N,N-diisopropyl)phosphoramidito-5-dimethoxytrityl-2-deox)-β-D-ribofuranosyl)-3-(4-acetoxybut-1-yn-1-yl)-1H-pyrazolo[3,4-d]pyrimidin-4(5H)-one (12)

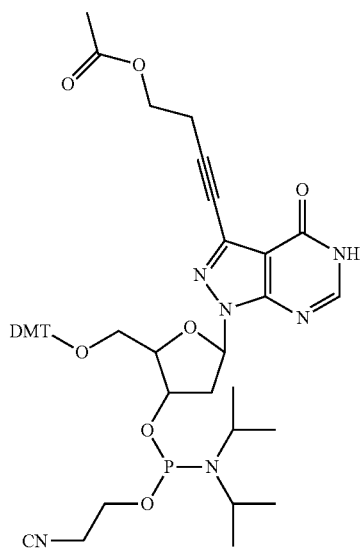

In a 500 mL flask were suspended 11 (2.8 g, 4.2 mmol) and diisopropylammonium tetrazolide (0.79 g, 4.6 mmol) in anhydrous CH₂Cl₂ (75 mL), then added 2-cyanoethyl N,N,N',N'-tetraisopropylphosphordiamidite (1.85 mL, 5.9 mmol) and stirred 14 h. The reaction was concentrated and dissolved in ethyl acetate, washed with 5% NaHCO₃(aq), brine, dried over Na₂SO₄, and concentrated to a yellow oil. The crude product was dissolved in anhydrous ethyl acetate and precipitated with anhydrous pentane; the precipitation was repeated, and the resulting gum was dried to obtain 12 as a white foam (3.3 g, 92% yield).

Example 3

This example illustrates the synthesis of the synthesis of the protected inosine 5'-phosphoramidite 16.

9-(5-(tert-Butylmethylsilyl)-3-dimethoxytrityl-2-deoxy-β-D-ribofuranosyl)-hypoxanthine (14)

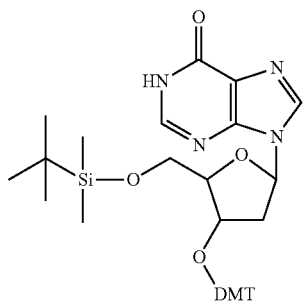

In a 125 mL flask, deoxy inosine (13) (1.5 g, 6 mmol) was suspended in anhydrous DMF (25 mL) and pyridine (10 mL), then added tert-butyldiphenylchlorosilane (1.82 g, 6.6 mmol) and stirred 12 hours. The reaction was titrated with additional silane until approximately equal amounts of starting material and bis-silane were present. The reaction mixture was concentrated to obtain an oil and added 5% NaHCO₃(aq) to form a white solid which was filtered, rinsing with water to remove starting material. The crude product was dissolved in DMF and pyridine, concentrated to remove moisture, then dissolved in anhydrous pyridine and added dimethylaminopyridine (100 mg, catalytic), 4,4'-dimethoxytrityl chloride (2.24 g, 6.6 mmol), and stirred for 72 hours. Concentrate and partition between ethyl acetate and water. Wash the aqueous layer with 10% citric acid, saturated NaHCO₃(aq), brine, dry over MgSO₄, and concentrate to an orange foam. Purify the crude product by flash chromatography using 33% acetone in dichloromethane to obtain 14 as a yellow-orange amorphous solid (3.5 g, 73% yield).

9-(3-Dimethoxytrityl-2-deoxy-β-D-ribofuranosyl)-hypoxanthine (15)

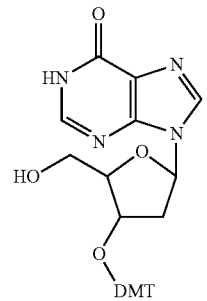

In a 125 mL flask, 14 (3.5 g, 4.4 mmol) was suspended in THF (20 mL) to form a slurry. Tetrabutylammonium fluoride in THF (8.8 mL, 1 M) was added along with an additional 10 mL THF and the mixture became a solution which was stirred for 14 h. The completed reaction was concentrated and purified by flash chromatography using 0-5% CH₃OH in CH₂Cl₂ to obtain 15 as a pale yellow solid (1.84 g, 75% yield).

9-(5-(2-Cyanoethyl-N,N-diisopropyl)phosphoramidito-3-dimethoxytrityl-2-deoxy-β-D-ribofuranosyl)-hypoxanthine (16)

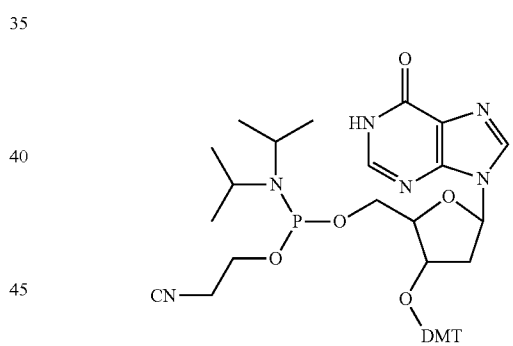

In a 125 mL flask, 15 (0.92 g, 1.66 mmol) was dissolved in anhydrous CH₂Cl₂ (20 ml), then added diisopropylammonium tetrazolide (313 mg, 1.8 mmol) and 2-cyanoethyl N,N,N',N'-tetraisopropylphosphordiamidite (783 µL, 2.5 mmol) and the reaction titrated with additional phosphoramidite reagent to completion. The suspension was concentrated and dissolved in ethyl acetate, washed with 5% NaHCO₃(aq), brine, dried over Na₂SO₄, and concentrated to an oil. The crude product was dissolved in anhydrous ethyl acetate and precipitated with anhydrous pentane; the precipitation was repeated and the resulting gum was dried to obtain 16 as an amorphous solid (715 mg, 57% yield).

Example 4

This example illustrates the preparation of 3-aminoalkynyl-substituted 1H-pyrazolo[3,4-d]pyrimidin-4(5H)-one phosphoramidites 18, 20, 22 and 24 and their incorporation into oligonucleotides.

General Procedure for the preparation of compounds 17, 19, 21 and 23, shown below.

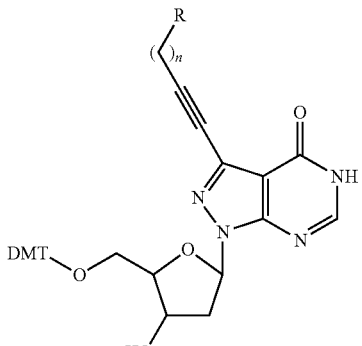

17
n = 1  R = RNCOCF$_3$ 19
n = 2  R = NHCOCF$_3$

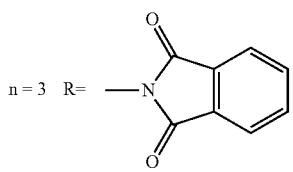

21

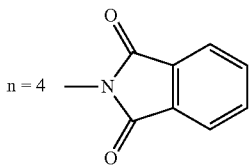

23

Solution of compound 10, protected aminoalkynes (3.0 eq), and triethylamine (3.5 eq) in anhydrous dimethylformamide (6.8 ml/mmol), (1.075 ml, 0.781 g, 7.72 mmol) was deoxygenated by argon flow and sonication (5 min). Pd(PPh$_3$)$_4$ (0.1 eq) and CuI (0.2 eq) were added and resultant mixture was magnetically stirred under argon at +60° C. Resultant mixture was concentrated in vacuum and residue was diluted with EtOAc. Resultant solution was washed with 10% citric acid, saturated aqueous sodium bicarbonate, and brine. Organic phase was separated, dried over MgSO$_4$, filtered from drying agent, and concentrated in vacuum. Residue was purified by flash column chromatography (silica gel, EtOAc) to give products 17 (3.5 h reaction time, 81% yield), 19 (1 h reaction time, 77% yield), 21 (2.5 h reaction time, 88% yield) and 23 (2.5 h reaction time, 88% yield).

General procedure for the preparation of compounds 18, 20, 22 and 24, shown below.

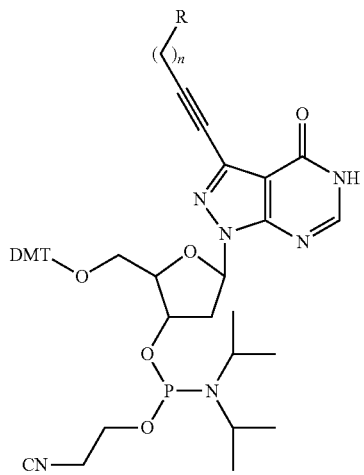

18
n = 1  R = RNCOCF$_3$ 20
n = 2  R = NHCOCF$_3$

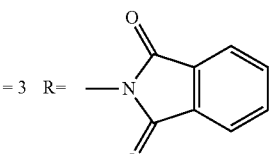

22

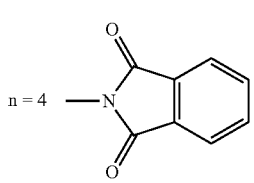

24

2-Cyanoethyl N,N,N'N'-tetraisopropylphoshordiamidite (1.4 eq) was added to mixture of substrate and diisopropylammonium tetrazolide (0.9 eq) in dry dichloromethane (13 ml/mmol). Resultant mixture was magnetically stirred under argon at room temperature. Reaction was quenched with saturated aqueous sodium bicarbonate and extracted with DCM. Organic phase was separated, dried over MgSO$_4$, filtered from drying agent, and concentrated in vacuum. Residue was dissolved in ether and added dropwise into stirred hexane. The liquid was decanted from oily precipitate, which was then dissolved in ether and precipitated in hexane one more time. Final residue was dried in vacuum to give products 18 (4 h reaction time, 98% yield), 20 (2 h reaction time, 91% yield), 22 (12 h reaction time, 87% yield), 24 (2 h reaction time, 74% yield).

Example 5

This example illustrates the preparation of 3-methycarbomoyloalkynyl-substituted (2-deox)-β-D-ribofuranosyl)-1H-pyrazolo[3,4-d]pyrimidin-4(5H)-one 5'-phosphoramidites 31, 32 and 33 and their incorporation into oligonucleotides.

General Procedure for the Preparation of Compounds 25, 26 and 27:

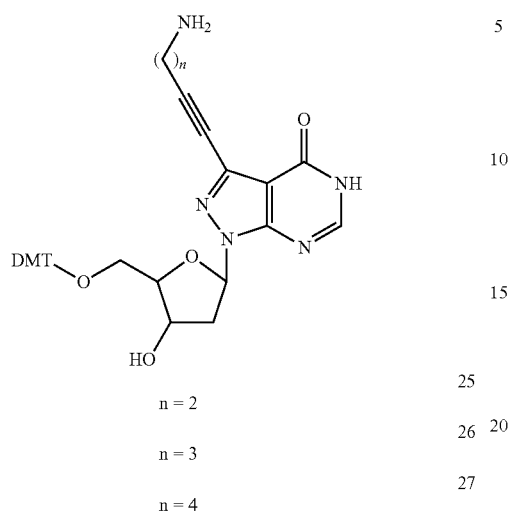

25 n = 2
26 n = 3
27 n = 4

A 100 ml Parr bomb was charged with 3.85 mmol of one of the compound 19, 21 or 23. Concentrated ammonium hydroxide (15 ml) and 40% aqueous methylamine (15 ml) were added and the bomb was sealed. After being stirred at 55° C. for 1 h the reaction mixture was cooled and concentrated. The resulting solid was washed with water and dried under vacuum to afford sufficiently pure product (~90% yield).

General Procedure for the Preparation of Compounds 28, 29 and 30:

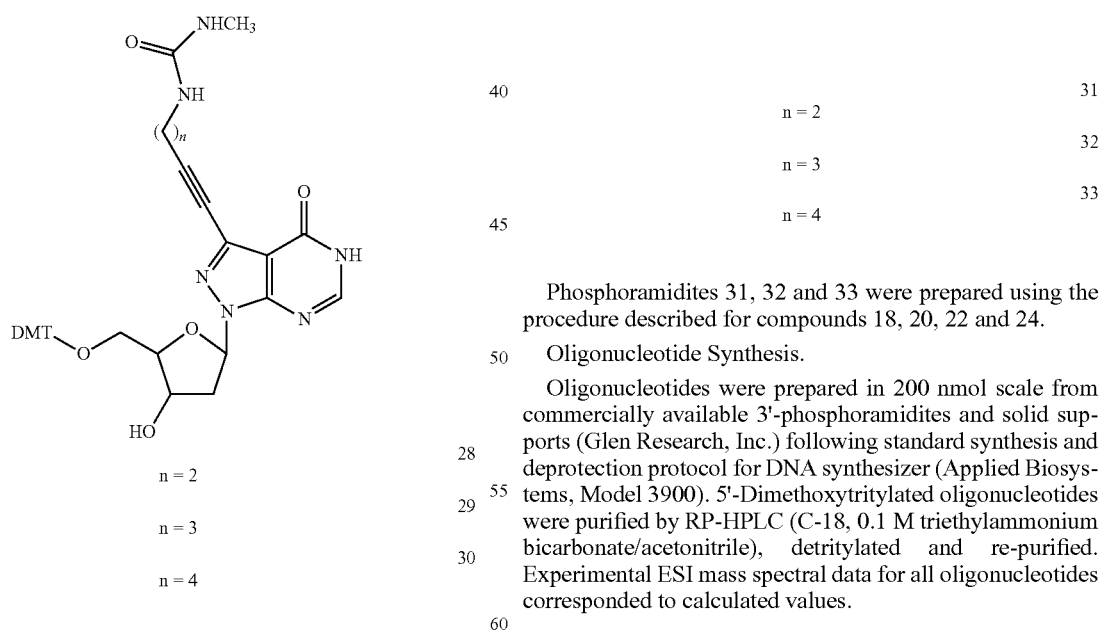

28 n = 2
29 n = 3
30 n = 4

To a solution of one of the amine-modified intermediate 25, 26 or 27 (0.46 mmol) in 5 ml of DMF was added diisopropylethylamine (0.92 mmol) followed by N-succinimidyl N-methylcarboxamide (0.92 mmol). The reaction was stirred at room temperature overnight and then concentrated. The resulting material was taken up into ethyl acetate, washed with saturated NaHCO$_3$, saturated NaCl and dried over MgSO$_4$. The residue obtained after solvent evaporation was chromatographed on silica eluting with a gradient (5-10%) of MeOH in dichloromethane. Concentration of the pure product fractions afforded compounds 28, 29 or 30 in 70-80% yields.

General Procedure for the Preparation of Phosphoramidites 31, 32 and 33:

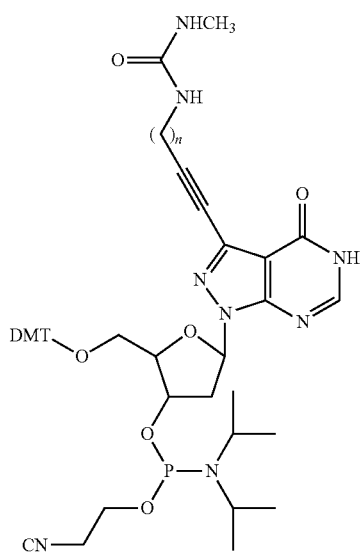

31 n = 2
32 n = 3
33 n = 4

Phosphoramidites 31, 32 and 33 were prepared using the procedure described for compounds 18, 20, 22 and 24.

Oligonucleotide Synthesis.

Oligonucleotides were prepared in 200 nmol scale from commercially available 3'-phosphoramidites and solid supports (Glen Research, Inc.) following standard synthesis and deprotection protocol for DNA synthesizer (Applied Biosystems, Model 3900). 5'-Dimethoxytritylated oligonucleotides were purified by RP-HPLC (C-18, 0.1 M triethylammonium bicarbonate/acetonitrile), detritylated and re-purified. Experimental ESI mass spectral data for all oligonucleotides corresponded to calculated values.

Example 6

This example illustrates the preparation of oligonucleotides containing 3-guanidinooalkynyl-substituted (2-deoxy-β-D-ribofuranosyl)-1H-pyrazolo[3,4-d]pyrimidin-4(5H)-ones I4g and I6g.

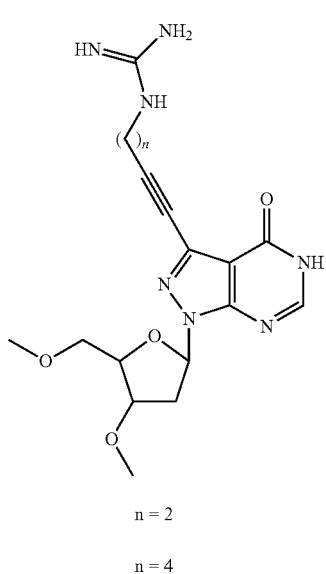

14g n = 2

16g n = 4

Oligonucleotides that contained modifications I4g and I6g (FIG. 1 and FIG. 9) were synthesized according to Roig, V.; Asseline, U. J. Am. Chem. Society, 2003, 125, 4616-4617 by a treatment of amine-modified oligonucleotide precursors (25 nmol) with 0.11 M solution of 1-pyrazole-1-carboxamidine hydrochloride in 1 M $Na_2CO_3$ (30 ul) for 1 day at room temperature. The modified oligonucleotides were purified by C18 reverse phase chromatography in a gradient of acetonitryl in 0.1 M triethylammonium bicarbonate buffer. The identity and purity of all modified oligonucleotides were confirmed by mass spectroscopy.

Example 7

This example illustrates the performance of 3-substituted-1H-pyrazolo[3,4-d]pyrimidin-4(5H)-one bases of the invention compared to that of hypoxanthine when substituted in oligonucleotides in duplex formation.

Duplex Melting Temperature Determination.

The melting temperature was determined by combining the 3-alkynyl-1H-pyrazolo[3,4-d]pyrimidin-4(5H)-one analogue-containing oligonucleotides with natural complements, with one experiment each for inosine analogue paired with adenine, cytosine, guanidine, and thymidine. The oligonucleotides containing inosine analogue were measured in three formats: 1) inosine analogue in the 6 position, measured from the 5'-end of the oligonucleotide; 2) inosine analogue in the 9 position, measured from the 5'-end of the oligonucleotide; 3) inosine analogue in both the 6 and positions, measured from the 5'-end of the oligonucleotide.

| Sequence (5'-3') | X position | SEQ ID NO: |
|---|---|---|
| GTAAGXAGACATAAC | 6 | 2 |
| GTAAGTAGXCATAAC | 9 | 3 |
| GTAAGXAGXCATAAC | 6 + 9 | 1 |

Oligonucleotides were combined in equimolar 2 µM concentrations in buffer containing 100 mM NaCl, 10 mM $MgCl_2$, and 10 mM Na-PIPES (pH 7). The solutions in 1 cm cuvettes were brought to 80° C. briefly then the temperature lowered to 15° C. Measurements were conducted on a Cary Bio 400 UV-Vis spectrophotometer equipped with a thermal peltier cell block and temperature probe. The temperature was ramped at a rate of 0.8° C./m in from 15 to 75° C. with the wavelength monitored at 268 nm. The melting temperature was calculated as the midpoint between the baselines of the associated and dissociated portions of the melting curve.

Melting temperatures of the studied duplexes are shown in FIGS. 10, 11, 12, and 13.

It can be seen that the duplexes containing analogues of the invention substituted for a base opposite A, T and C in a generally more stable than the duplex the duplexes containing deoxy inosine. In the case of G similar $T_m$s are observed for both deoxyinosine and the analogues of the invention.

It is also observed that the aminobutynyl-substituted analog (I07) stabilizes A, T and C pairs greater than any other studied analogues.

Example 8

This example (with results shown in FIGS. 14 and 15) illustrates the ability of 3-(hydroxybutynyl)-1H-pyrazolo[3,4-d]pyrimidin-4(5H)-one and 3-(aminobutynyl)-1H-pyrazolo[3,4-d]pyrimidin-4(5H)-one-substituted PCR primers to efficiently participate in amplification reactions. It was further demonstrated that both hydroxybutynyl and aminobutynyl-substituted analogues performed better than 2'-deoxyinosine when substituted in a primer.

Real-time PCR was conducted on an ABI Prism® 7900 Sequence Detection System (SDS) (Applied Biosystems, Foster City, Calif.), 50 cycles of a two step PCR (95° C. for 15 s, 65° C. or 70° for 30 s) profile was run, after an initial 15 min at 95° C. Commercially available 2× Qiagen QuantiTect Probe PCR Master mix (Qiagen cat.#204345) was used. Final concentration of both primers was 0.5 µM. Each 20 µl reaction contained 10 ng of template DNA. Routinely DNA samples were tested in triplicates using a 384-well plate.

Primers.

An adenovirus assay was developed using a fluorogenic reverse flap primer (US Application No. 2007-0048758) which contained a minor groove binder ligand ($DPI_3$) and fluorescein (FAM) as a fluorescent label. The forward primer contained deoxyinosine, hydroxybutynyl (I04) or aminobutynyl (I07)-substituted 1H-pyrazolo[3,4-d]pyrimidin-4(5H)-one nucleosides in various positions (FIGS. 14 and 15). An unmodified forward primer was also utilized as a positive control.

Example 9

This example (with results shown in FIG. 16) illustrates the ability of multiple substitutions of the 3-(hydroxy butynyl)-1h-pyrazolo[3,4-d]pyrimidin-4(5h)-one and 3-(aminobutynyl)-1h-pyrazolo[3,4-d]pyrimidin-4(5h)-one-substituted PCR primers to efficiently participate in the amplification of Meticillin-resistant Staphylococcus aureus LGA251 target.

PCR is performed using the final concentrations of the assay components in the reaction mixture is the dT(8)-AP593 passive control. 0.035 µM, forward primer 1.260 µM, reverse primer 0.500 µM, probe 0.200 µMm 1× enhancer, 1×Tfi PCR Master Mix (Life Science Technologies, Inc) contains all the reagents necessary to perform PCR including uracil-N-glycosylase (UNG). Twenty microliters of the mixture was introduced in a 96 well PCR plate with 10 µl of sample nucleic acid. The plate was sealed with MicroAmp® Optical Adhesive Film (Applied Biosystems, Foster City, Calif.) and then centrifuged to collect the assay solution in the bottom of the plate well. The assay was then performed in an ABI 7500 DX Fast Block Real-time PCR machine with the protocol shown in Table I below.

TABLE 1

ABI 7500DX Fast Block real-time PCR protocol

| Stage | Time | Temperature |
|---|---|---|
| UNG | 2 min | 50° C. |
| Denature | 2 min | 93° C. |
| PCR Cycling | 10 sec | 93° C. |
| (45X) | 30 sec | 56° C. |
|  | 20 sec | 72° C. |
| Total Time | 1 hr 10 min |  |

It can be seen that the duplex containing the 3-(hydroxybutynyl)-1H-pyrazolo[3,4-D]pyrimidin-4(5H)-one is-substituted for three A's and two T's, amplified well at 56° and 60° C. with cts of 36 and 36 respectively. In contrast the same substitutes with inosine, only amplified at 56° C. with a Ct of 42. In the case of G, similar $T_m$s are observed for both deoxyinosine and the analogues of the invention. this illustrate that primers with multiple aminobutyl substitutions amplify well at 60° C. while a primer similarly substituted with inosines did not amplify at this temperature. this again confirms that ability of aminobutyl analog of the invention to stabilize duplexes when substituted; in this case for A and T.

Example 10

This example illustrates that when 3-(3-(hydroxybutynyl)-1H-pyrazolo[3,4-D]pyrimidin-4(5h)-one is substituted for T in a primers it is recognized by the polymerase as a G and that C is incorporated as the complementary base in the synthesized amplicon.

PCR was performed as described in Example 9. The target sequence and primer sequences are shown in FIG. 17. The amplicons obtained from amplification with the natural primer, the F(dI) primer and the F(I07) primer were submitted for sequencing analysis. The sequences of the amplicons generated by these primers are shown in FIG. 17. The amplicon generated by the natural primer incorporated two As complementary to the Ts in the primers. However, with the F(dI) primer and the F(I07) primer two Cs were incorporated in each case. Therefore DNA polymerase incorporated a C complementary to the inosine and the aminobutylinosine.

REFERENCES

U.S. Patent Documents

U.S. Pat. No. 3,996,345
U.S. Pat. No. 4,351,760
U.S. Pat. No. 5,177,196
U.S. Pat. No. 5,419,966
U.S. Pat. No. 5,492,806
U.S. Pat. No. 5,512,677
U.S. Pat. No. 5,525,464
U.S. Pat. No. 5,539,082
U.S. Pat. No. 5,556,752
U.S. Pat. No. 5,585,481
U.S. Pat. No. 5,696,251
U.S. Pat. No. 5,714,331
U.S. Pat. No. 5,736,626
U.S. Pat. No. 5,766,855
U.S. Pat. No. 5,773,571
U.S. Pat. No. 5,801,155
U.S. Pat. No. 6,312,894
U.S. Pat. No. 6,727,356
U.S. Pat. No. 6,790,945
U.S. Pat. No. 7,045,610
U.S. Pat. No. 7,348,146
U.S. Pat. No. 7,319,022
U.S. Pat. No. RE 38,416

International Patent Documents

International Patent Publication WO92/10588
International Patent Publication WO96/17957

Other Publications

Ausubel, et al., Current Protocols In Molecular Biology, John Wiley & Sons (1987, 1988, 1989, 1990, 1991, 1992, 1993, 1994, 1995, 1996)

Beaucage and Iyer, Tetrahedron 48:2223-2311 (1992)

Bergstrom et al, Nucl. Acids. Res., 25: 1935-1942 (1997)

Chen et al., Nucl. Acids Res., 23:2662-2668 (1995)

Eckstein (ed.), Oligonucleotides and Analogues: A Practical Approach, IRL Press (1991)

Gait (ed.), Oligonucleotide Synthesis: A Practical Approach, IRL Press (1984)

Graig. J. Mol. Biol. 19: 548-555 (1966)

T. W. Greene and P. G. Futs, Protective Groups in Organic Chemistry, (Wiley, 2nd ed. 1991)

Harrison and Harrison et al. Compendium of Synthetic Organic Methods, Vols. 1-8 (John Wiley and Sons. 1971-1996)

Haugland. R. P., Handbook of Fluorescent Probes and Research Chemicals, Sixth Edition. Molecular Probes. Eugene, Oreg. 1996

Lee H et al. Methods Mol. Biol. 855: 155-74, 2012

Loakes et al., J. Mol. Biol. 270: 426-435 (1997)

Loakes. Nucl. Acids Res. 29: 2437-2447 (2001)

Ming et al., Nucl. Acids Symp. Series No. 52: 471-472 (2008)

Nielsen et al., Science 254:1497-1500 (1991)

Niemz. A. et al Trends Biotechnol., 29: 240-50 (2011)

Palissa et al., Z. Chem. 27:216 (1987)

Reddy, B. S. P., Dondhi, S. M. and Lown, J. W., *Pharmacol. Therap.*, 84:1-111 (1999)

Sambrook, Fritsch & Maniatis, MOLECULAR CLONING: A LABORATORY MANUAL, Second Edition, Cold Spring Harbor Laboratory Press (1989)

Singh et al. Chem. Comm. 455-456 (1998)

Uhlmann et al. Angew. Chem. Int. Ed. 37:2796-2823 (1998)

Walker, W. L., Kopka, J. L. and Goodsell, D. S., *Biopolymers*, 44:323-334 (1997)

Watkins and SantaLucia, Nucleic Acids Res., 23: 62588-6267 (2005)

Wemmer, D. E., and Dervan P. B., *Current Opinion in Structural Biology*, 7:355-361 (1997)

Wengel J., Acc. Chem. Res., 32:301-310 (1998)

Zimmer, C & Wahnert, U. *Prog. Biophys. Molec. Bio.* 47:31-112 (1986)

What is claimed is:

1. A method for the polynucleotide amplification of target nucleic acid sequences comprising:
    a) providing a mixture including a sample containing one or more target nucleic acids and at least one oligonucleotide that is substantially complementary to a target nucleic acid sequence, wherein the target nucleic acids comprise the target nucleic acid sequence and at least one target nucleic acid sequence variation, wherein the target nucleic acid sequence variation differs from the target nucleic acid sequence by at least one polymorphic base, wherein the at least one polymorphic base is A, C, or T,
        wherein said oligonucleotide comprises at least one 3-alkynyl-1H-pyrazolo[3,4-d]pirimidine-4(5H)-one analogue positioned opposite the at least one polymorphic base that forms a mismatched duplex with the target nucleic acid sequence and the target nucleic acid sequence variation having substantially the same stability as a complementary duplex, regardless which polymorphic base is positioned opposite to the 3-alkynyl-1H-pyrazolo[3,4-d]pirimidine-4(5H)-one base;
    b) incubating the mixture under hybridization conditions, wherein the hybridization conditions comprise conditions favorable for polymerization and wherein the at least one oligonucleotide hybridizes to the target nucleic acid sequence and the target nucleic acid sequence variation to form mismatched duplexes having substantially the same stability as a complementary duplex, to produce amplified target nucleic acids from the target nucleic acid sequence and the target nucleic acid sequence variation; and
    c) detecting the amplified target nucleic acids, wherein the amplified target nucleic acids are not distinguished.

2. The method of claim 1,
    wherein the at least one oligonucleotide comprises one or more than one oligonucleotide primers and a detectable nucleic acid oligomer probe of between 5 and 100 bases,
    wherein said detectable nucleic acid oligomer probe or at least one of said oligonucleotide primers has a backbone component selected from the group consisting of a sugar phosphate backbone, a modified sugar phosphate backbone, a locked nucleic acid backbone, a peptidic backbone, or a variant thereof, wherein said nucleic acid oligomer probe has a sequence substantially complementary to a probe region of at least one of the target nucleic acid sequences, wherein at least one of said oligonucleotide primers has a sequence complementary to a portion of at least one of the target nucleic acid sequences or complementary to an adjacent or overlapping portion of the probe region of at least one of the target nucleic acid sequences, and wherein said nucleic acid oligomer probe or one or more of said oligonucleotide primers has at least one nucleic acid base substituted with a 3-alkynyl-1H-pyrazolo[3,4-d]pyrimidin-4(5H)-one analogue.

3. The method of claim 2, wherein the polynucleotide amplification is continuously monitored by detecting hybridization of nucleic acids, wherein the hybridization of nucleic acids is identified by detecting hybridization of the nucleic acid oligomer probe to the amplified target, or by extending at least one of the oligonucleotide primers with the polymerizing enzyme.

4. The method of claim 1, wherein the polynucleotide amplification is performed by a polymerizing enzyme under isothermal conditions.

5. The method of claim 2, wherein more than one of said nucleic acid oligomer primers have at least one nucleic acid base substituted with a 3-alkynyl-1H-pyrazolo[3,4-d]pyrimidin-4(5H)-one analogue.

6. The method of claim 2, wherein at least one of said oligonucleotide primers further comprises a covalently attached minor groove binder ligand.

7. The method of claim 2, wherein the detectable nucleic acid oligomer probe further comprises one or more of a covalently attached minor groove binder ligand, a fluorophore, and a quencher.

8. The method of claim 1, wherein the 3-alkynyl-1H-pyrazolo[3,4-d]pyrimidin-4(5H)-one analogue comprises Formula III or Formula IV:

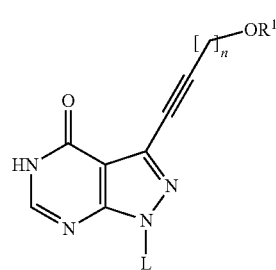

Formula III

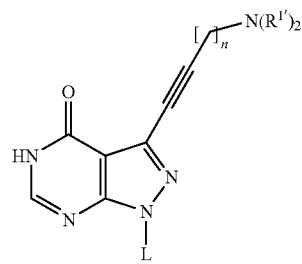

Formula IV wherein:

$R^1$ is H;

$R^{1'}$ is H;

L is a sugar or sugar/phosphate backbone analogue, including but not limited to a backbone of DNA, RNA, PNA, locked nucleic acid, modified DNA, modified PNA, modified RNA, or any combination thereof; and n is 1 to 5.

9. The method of claim 2, wherein the measured threshold cycle number (Ct) from the amplified target nucleic acid is similar to the Ct when unsubstituted primers are used.

10. The method of claim 2, wherein the oligonucleotide primers comprise nucleic acid bases that are normal bases, 3-alkynyl-1H-pyrazolo[3,4-d]pyrimidin-4(5H)-one analogues, and modified bases, wherein at least one of the oligonucleotide primer comprises at least one 3-alkynyl-1H-pyrazolo[3,4-d]pyrimidin-4(5H)-one analogues and at least one modified base.

11. The method of claim 1 wherein the sample comprises a plurality of polynucleotides containing the one or more target nucleic acid sequences.

12. The method of claim 2, wherein the one or more oligonucleotide primers are between 5 and 50 bases.

* * * * *